(12) United States Patent
Muderlak et al.

(10) Patent No.: US 6,467,651 B1
(45) Date of Patent: Oct. 22, 2002

(54) SYSTEM AND METHOD FOR DISPENSING SOAP

(75) Inventors: Kenneth J. Muderlak, Shorewood, WI (US); Rocky Shieh, Hsin Chu (TW)

(73) Assignee: Technical Concepts, L.P., Mundelein, IL (US)

( * ) Notice: Subject to any disclaimer, the term of this patent is extended or adjusted under 35 U.S.C. 154(b) by 0 days.

(21) Appl. No.: 09/525,976

(22) Filed: Mar. 15, 2000

Related U.S. Application Data
(60) Provisional application No. 60/154,101, filed on Sep. 15, 1999, and provisional application No. 60/156,981, filed on Oct. 1, 1999.

(51) Int. Cl.[7] .................................................. B61D 5/08
(52) U.S. Cl. .............................. 222/52; 222/63; 222/333
(58) Field of Search ............................... 222/52, 63, 333

(56) References Cited

U.S. PATENT DOCUMENTS

| | | | | | |
|---|---|---|---|---|---|
| 4,917,265 A | * | 4/1990 | Chiang | ......................... | 222/52 |
| 5,249,718 A | * | 10/1993 | Muderlak | .................... | 222/642 |
| 5,836,482 A | * | 11/1998 | Ophardt et al. | ............. | 222/325 |
| 5,988,440 A | * | 11/1999 | Saunders et al. | ............. | 222/63 |
| 6,036,056 A | * | 3/2000 | Lee et al. | ..................... | 222/63 |

* cited by examiner

Primary Examiner—William C. Doerrler
Assistant Examiner—Frederick C. Nicolas
(74) Attorney, Agent, or Firm—Lee, Mann, Smith, McWilliams, Sweeney & Ohlson

(57) ABSTRACT

An automatic fluid soap dispensing apparatus and method comprising a dispensing spout, housing operatively connected to the dispensing spout and the housing adapted to removably receive and hold a fluid soap containing reservoir module in communication with the dispensing spout. The reservoir module has a central axis, and includes a pump mechanism and delivery tube mounted on the reservoir module in alignment with the central axis. The dispensing tube is adapted to move in the dispensing spout when the pump mechanism is actuated.

39 Claims, 23 Drawing Sheets

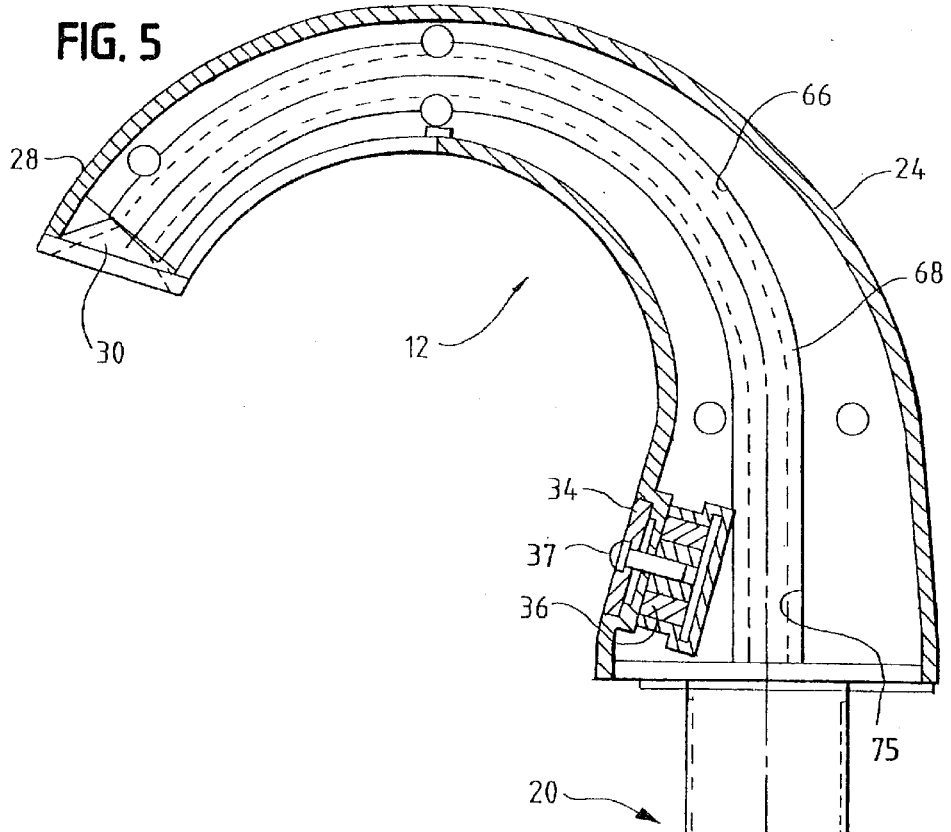
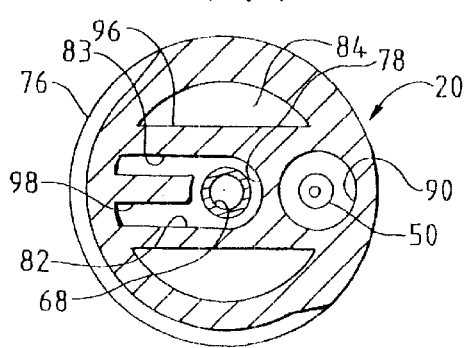

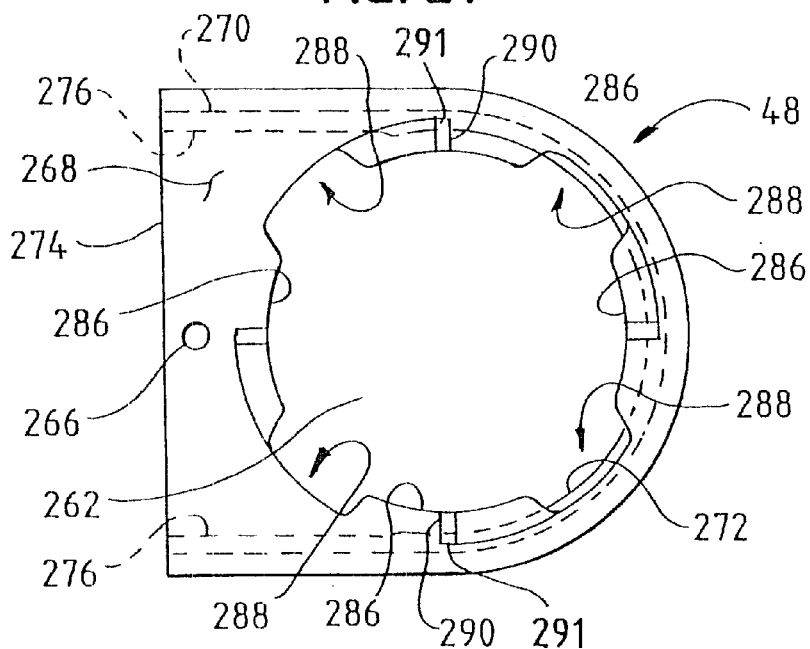
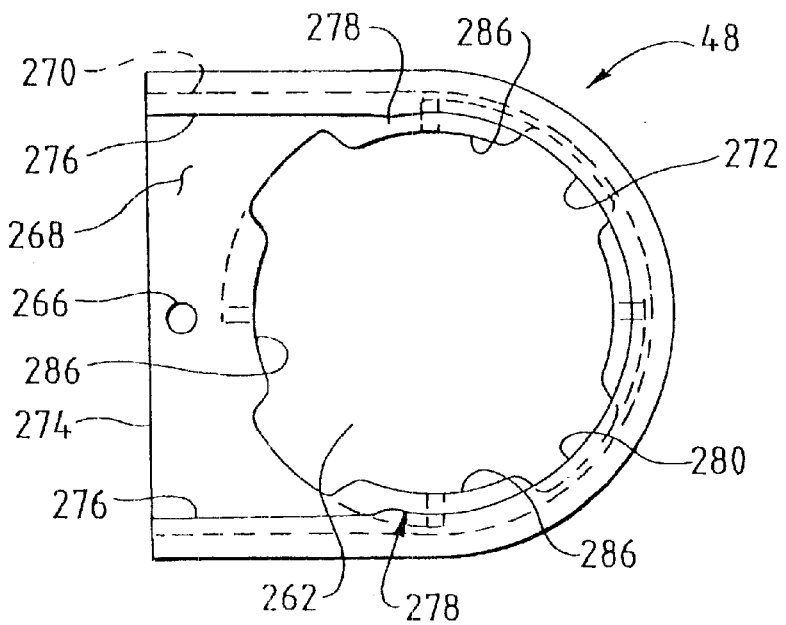

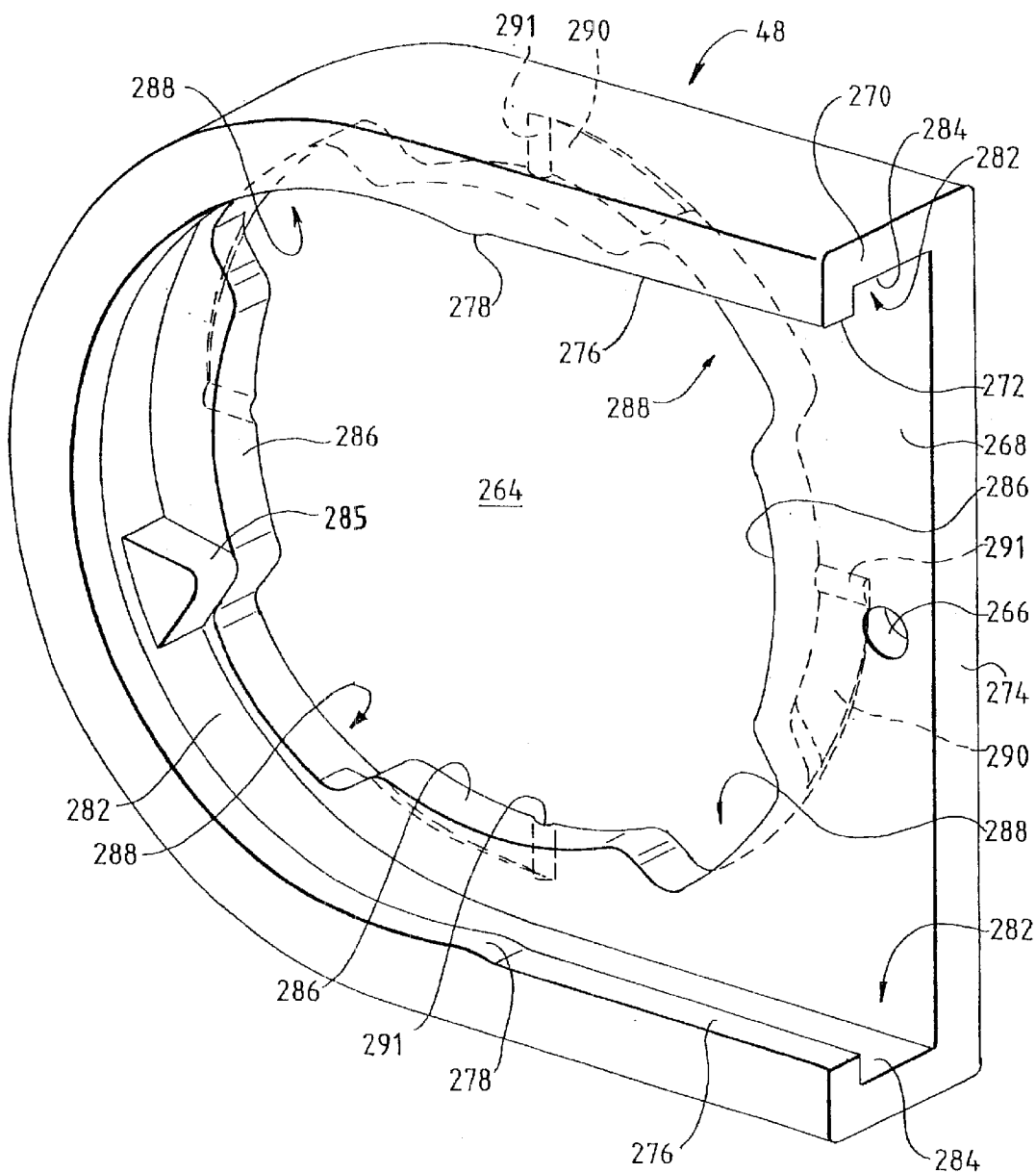

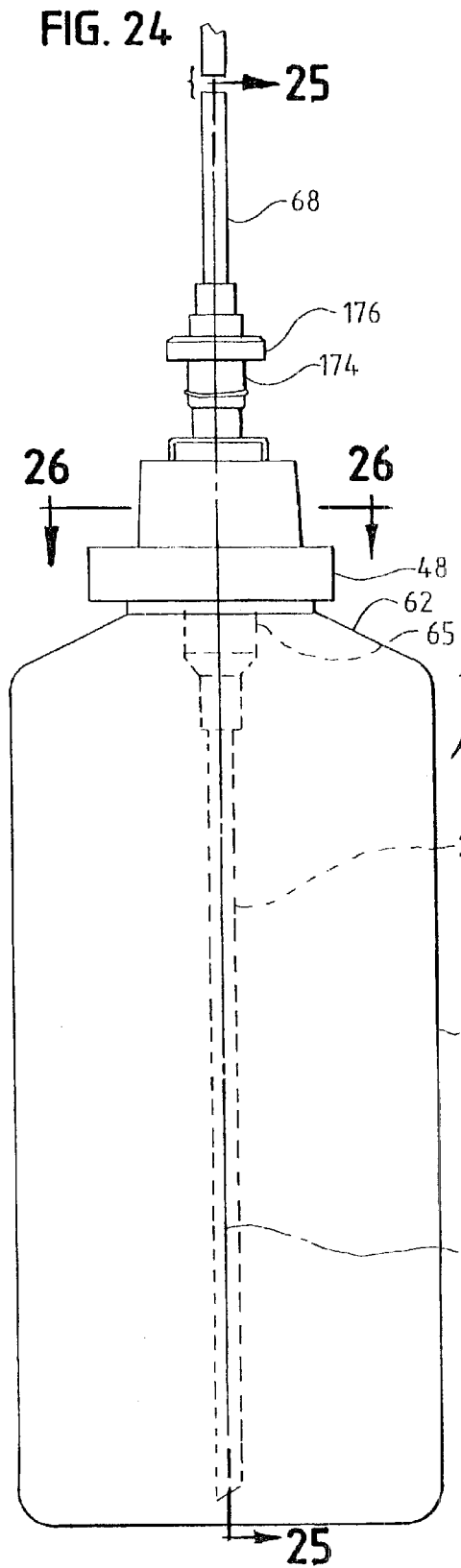
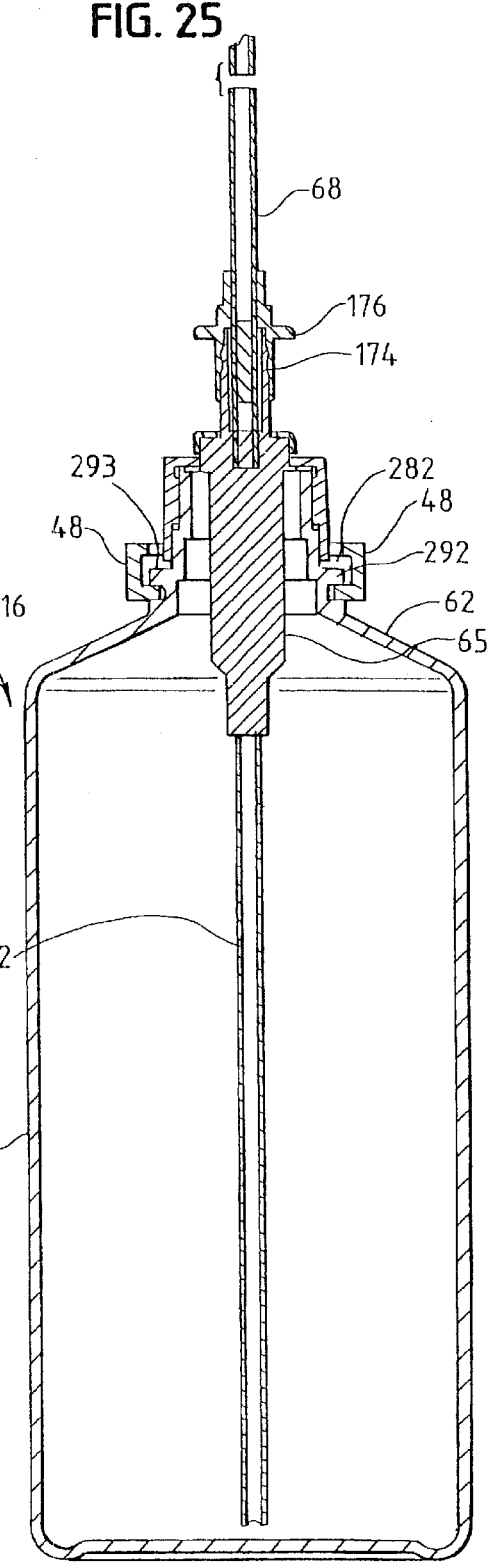

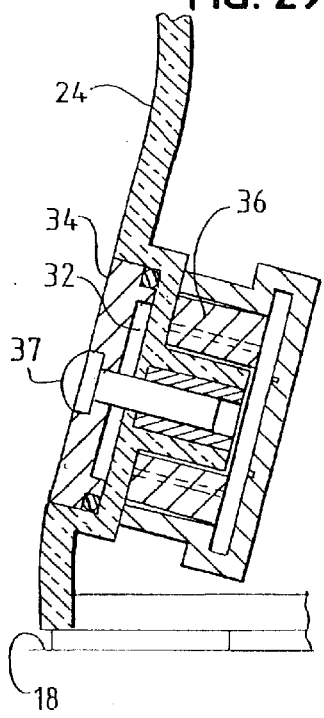
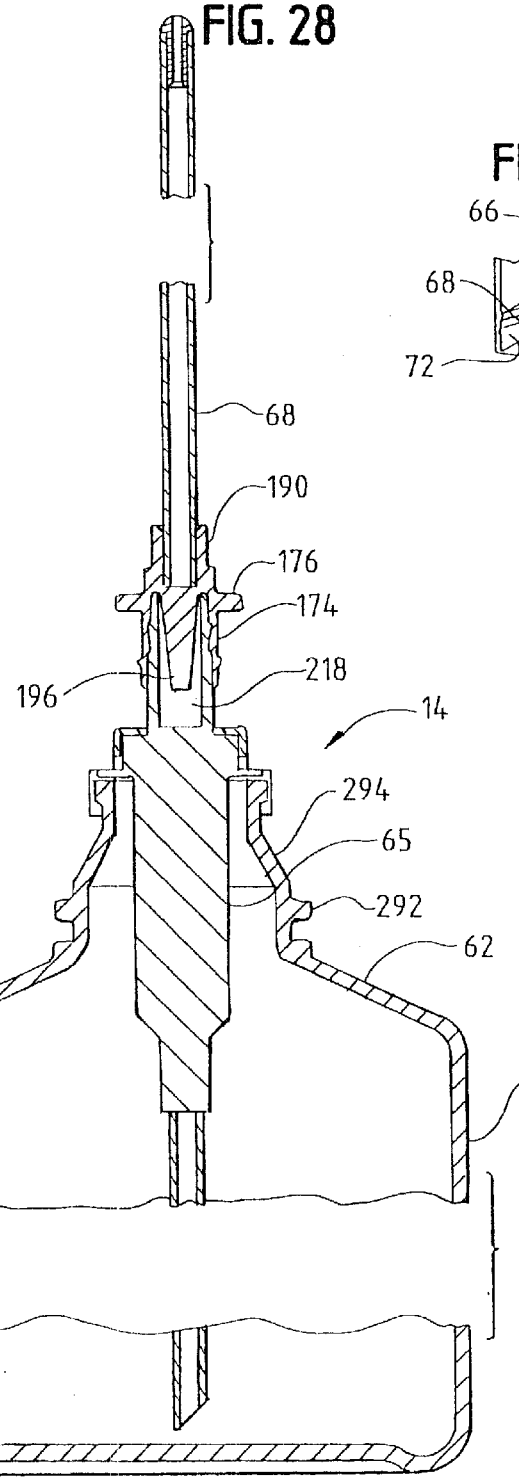
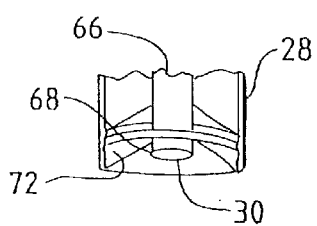

FIG. 32
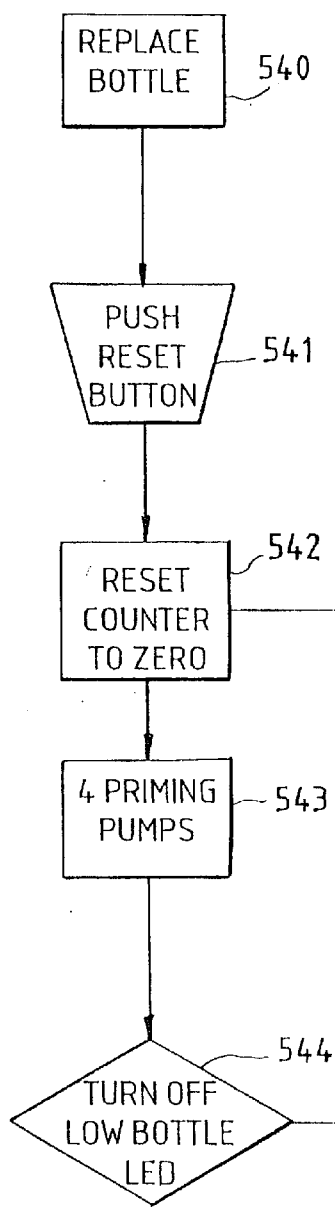
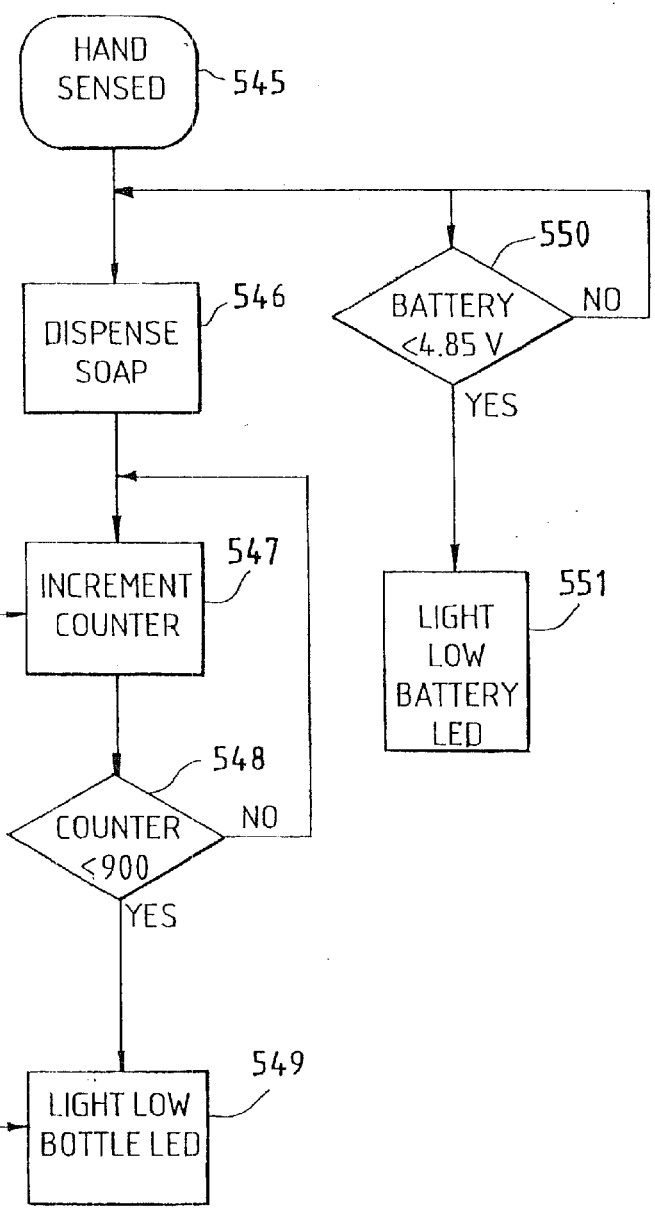

SYSTEM AND METHOD FOR DISPENSING SOAP

This patent claims the benefit of prior filed copending provisional applications having the provisional application No. 60/154,101 filed Sep. 15, 1999 and the provisional application No. 60/156,981 filed Oct. 1, 1999.

The invention relates generally to automatically operated devices to repeatedly dispense fluid material from a replaceable reservoir, and more particularly to a fluid dispensing apparatus and method that dispenses fluid material automatically in response to sensing the presence of a user.

BACKGROUND OF THE INVENTION

Users of modern public washroom facilities increasingly desire that each of the fixtures in the washroom operate automatically without being touched by the user's hands. This is important in view of increased user awareness of the degree to which germs and bacteria may be transmitted from one person to another in a public washroom environment. Today, it is not uncommon to find public washrooms with automatic, hands-free operated toilet and urinal units, hand washing faucets, soap dispensers, hand dryers and door opening mechanisms. This automation allows the user to avoid touching any of the fixtures in the facility, and therefore lessens the opportunity for the transmission of disease carrying germs or bacteria resulting from manual contact with the fixtures in the washroom.

It is also required that counter-mounted fluid soap dispensers in public washrooms include a soap reservoir that is readily replaceable when empty, and is inexpensive to manufacture and maintain. Therefore, it is desirable that the soap reservoir include a container that is easy to install in association with the permanent elements of the soap dispensing fixture, is held fast to the fixture, and is easy to remove from the fixture when empty, and functions in coordination with the operating elements of the fluid soap dispenser.

It is also desirable that a soap reservoir include a fluid soap delivery system that ensures the delivery of a uniform measured dose of fluid soap to a user upon each automatic actuation of the fixture. The reservoir and pump assembly must function as a unitary device to deliver consistent measures of fluid soap from the reservoir to the user.

Several automatically operated washroom fluid soap dispensers have been developed, as disclosed in U.S. Pat. No. 4,967,935 (Celest), U.S. Pat. No. 4,938,384 (Pilolla), U.S. Pat. No. 4,921,150 (Lagargren), U.S. Pat. No. 4,722,372 (Hoffman), and U.S. Pat. No. 4,645,094 (Acklin), by way of example. However, these devices do not incorporate structural elements that desirably provide consistent operation, ease of installation and replaceability, and low cost of manufacture.

SUMMARY OF THE INVENTION

The invention works towards overcoming the above problems in prior countertop fluid soap dispenser fixtures. The disclosed invention presents a fluid soap dispenser assembly that provides a consistent measured amount of fluid soap into the hands of a user. Towards this, an embodiment of the invention includes an elongated delivery tube directly connected to a reservoir container and pump assembly, which delivery tube moves axially within a rigid dispensing spout each time the fluid soap dispenser is actuated.

The soap delivery tube and pump assembly are centrally mounted on the top of a fluid soap reservoir container. As a result, a new delivery tube, pump assembly, and fluid soap container may be provided with a full soap reservoir assembly upon each replacement of an empty soap reservoir assembly. Moreover, as a result of the centrally disposed location of the elongated delivery tube and pump assembly on the reservoir container, the delivery tube may be readily extended axially through a curved, rigid dispensing spout mounted to the countertop, and the delivery tube may be readily rotated about its longitudinal axis for ease of movement in the dispensing spout when the unitary reservoir container, pump assembly and delivery tube assembly are rotated during installation of a new, full reservoir container and pump assembly.

The pump assembly mounted on the fluid soap reservoir of the invention also provides a pump actuator mechanism. The pump actuator mechanism may include a laterally extending actuator portion of the pump assembly. The actuator portion may permit the pump assembly and delivery tube to be mounted centrally with respect to the axis of the reservoir container and the soap dispenser fixture elements. The pump actuator mechanism is controlled by a battery operated or other power activated drive mechanism. The drive mechanism is activated upon the sensing of the presence of a user's hand at a position that is adjacent to the dispensing spout. This may be achieved by a reflective proximity sensor forming part of the soap dispensing fixture mounted above the countertop.

The fluid soap reservoir container and pump assembly of the invention also provides advantages over fluid soap dispensing systems of the prior art. A standard manufactured pump assembly may be used in the fabrication of the reservoir module of the invention due to the central position of the pump and of the dispensing tube relative to the soap container. This permits the reservoir module to be filled using standard bottle filling equipment found in the facilities of most contract bottle fillers. This application of standard equipment provides a substantial cost savings in the production of soap refill reservoir modules in accordance with the invention.

The central location of the pump assembly and delivery spout on the reservoir module also permits rapid installation of the reservoir module on the motor housing of the dispenser by a simple rotation of the soap reservoir and pump assembly to complete a bayonet-type connection with the fixed pump housing of the invention. Moreover, the construction of the reservoir and pump assembly enables the mass production of a reliable refill unit.

The combination of the rigid dispensing spout and fluid soap delivery tube moveable inside the spout permits economy of construction not found in prior automatic soap dispensers. The spring in the pump assembly mounted on the soap container provides the force to return the delivery tube to its start position after a dose of fluid soap has been dispensed. The spout configuration and construction is adapted to provide ease of movement of the delivery tube in the spout, with a minimum of friction produced. The elongated delivery tube of the invention is rigid enough to withstand hydraulic pressure developed during the dispensing operation, and flexible enough to move substantially frictionless relative to the interior of the dispensing spout.

The motor housing of the invention mounts to a shank extending through a countertop, such that the housing may be readily rotated away from the underside of the sink bowl, and away from plumbing fixtures. This is a result of the central mounting of the operative components extending from the reservoir module, through the motor housing, to the entrance to the dispensing spout.

The invention also includes indicators to advise a maintenance operator when the reservoir module is empty of fluid soap after a predetermined number of electronically metered doses of soap have been dispensed. A separate indicator advises when the system's batteries are low.

BRIEF DESCRIPTION OF THE DRAWINGS

FIG. 4 is a cross-sectional view of the threaded shank portion of the invention, taken along line 4—4 in FIG. 2;

FIG. 5 is a front elevation view of the rigid spout and support shaft of the automatic soap dispenser of the invention;

FIG. 21 is a bottom plan detail view of the mounting clip to removably attach the reservoir module and pump assembly to the motor housing and support assembly of the invention;

FIG. 22 is a top plan detail view of the mounting clip of FIG. 21;

FIG. 23 is a perspective detail view of the mounting clip of FIG. 23;

FIG. 24 is an assembly elevation of view of the reservoir module and pump assembly of the invention;

FIG. 25 is a section view of the reservoir module and pump assembly of FIG. 24, taken along line 25—25 of FIG. 24, with the pump mechanism shown only in outline;

FIG. 28 is a partial section view of the pump actuator mechanism and container neck of the invention;

FIG. 29 is a partial section view of the electric eye sensor installation of the invention;

FIG. 30 is a detail front elevation view of the outlet portion of the rigid spout of the invention;

FIG. 32 is a flow chart of an embodiment of the method of dispensing soap of the invention.

DETAILED DESCRIPTION OF THE ILLUSTRATED EMBODIMENTS

Figure 1:
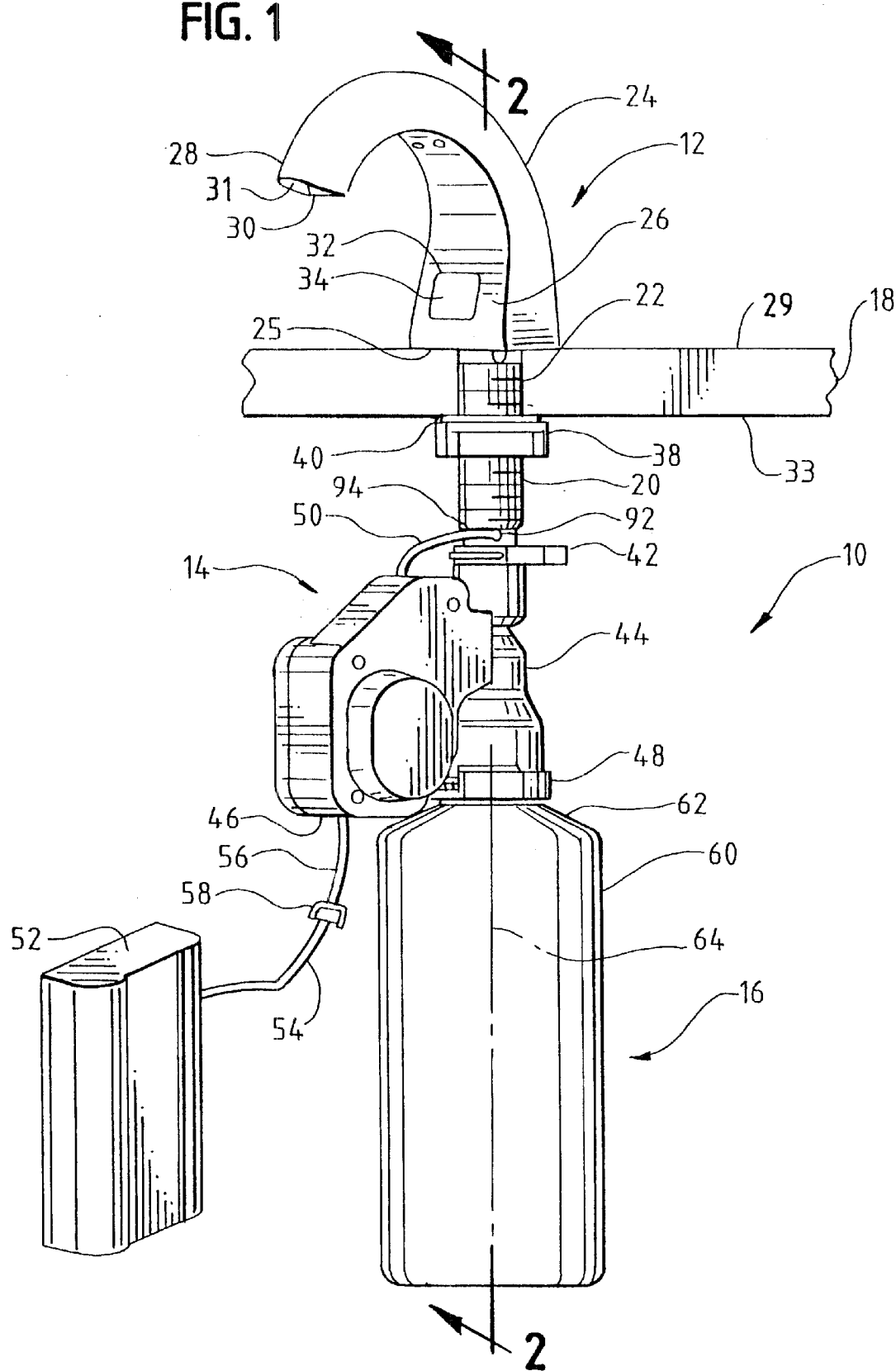
FIG. 1 is an elevation perspective view of the automatic soap dispenser of the invention, shown mounted in a washroom countertop.

Referring to FIG. 1, an automatic fluid soap dispensing system constructed in accordance with the invention is generally designated by the numeral 10. The fluid dispensing system 10 may include three major assemblies: a spout and mounting shaft assembly 12, a motor housing and support assembly 14, and a reservoir module and pump assembly 16. The fluid dispensing system 10 is shown mounted on a countertop 18 with a support shaft 20 extending through an aperture 22 extending, where the aperture 22 is disposed through the countertop 18. Countertop 18 may be a sink countertop and support shaft 20 may be hollow (hollow portion 84) and threaded (external threads 76).

Support shaft 20 is fixed to, or may form a part of, rigid spout 24. Rigid spout 24 may include a base 25 abutting countertop 18, an upwardly extending electronic eye housing portion 26, and a curved dispensing portion 28. In the illustrated embodiment of FIG. 2, a resilient pad 27 is disposed between base 25 of the spout 24, and the upper surface 29 of countertop 18. The outer end of curved dispensing portion 28 includes an indented outlet 30 (FIG. 1) having a spout opening 31 therein (FIG. 2) that may aid in dispensing soap. Housing portion 26 includes an opening 32 covered by a transparent lens 34 behind which an electric eye sensor (or assembly) 36 (FIG. 2) is mounted in the housing portion 26, as will be explained. Indicator lights 37 (FIG. 2) are also disposed behind transparent lens 34 to signal a "battery low" and/or soap reservoir "empty" condition. Indicator lights may be light emitting diodes (LEDs).

A manually rotatable internally threaded nut 38 engages the outer threads 76 of support shaft 20 with mating internal threads 77. When rotated upwardly, nut 38 draws base 25 of rigid spout 24 down and against pad 27 so as to form a tight fitting engagement with countertop 18. This may firmly mount spout and shaft assembly 12 to the countertop 18. A lock washer 40 may be inserted between nut 38 and the underside 33 of countertop 18. This arrangement may further assure that spout and shaft assembly 12 is firmly mounted to the countertop 18 to avoid movement of the spout 24.

Motor housing and support assembly 14 may include pump housing 44 and motor and actuator mechanism housing 46. Pump housing 44 includes a cylindrically hollow interior 47 (FIG. 2) through which fluid soap may be conveyed from reservoir and pump assembly 16 to opening 30 of spout 24, as will be explained. A reservoir assembly mounting clip 48 is located at the bottom of pump housing 44 to removably mount reservoir and pump assembly 16 to pump housing 44, as will be explained. Moreover, when fluid dispensing system 10 is fully assembled, motor housing and support assembly 14 may be removably attached to the lower end of support shaft 20 by a shank clip 42, as will be explained with reference to FIG. 8–12.

Figure 2:
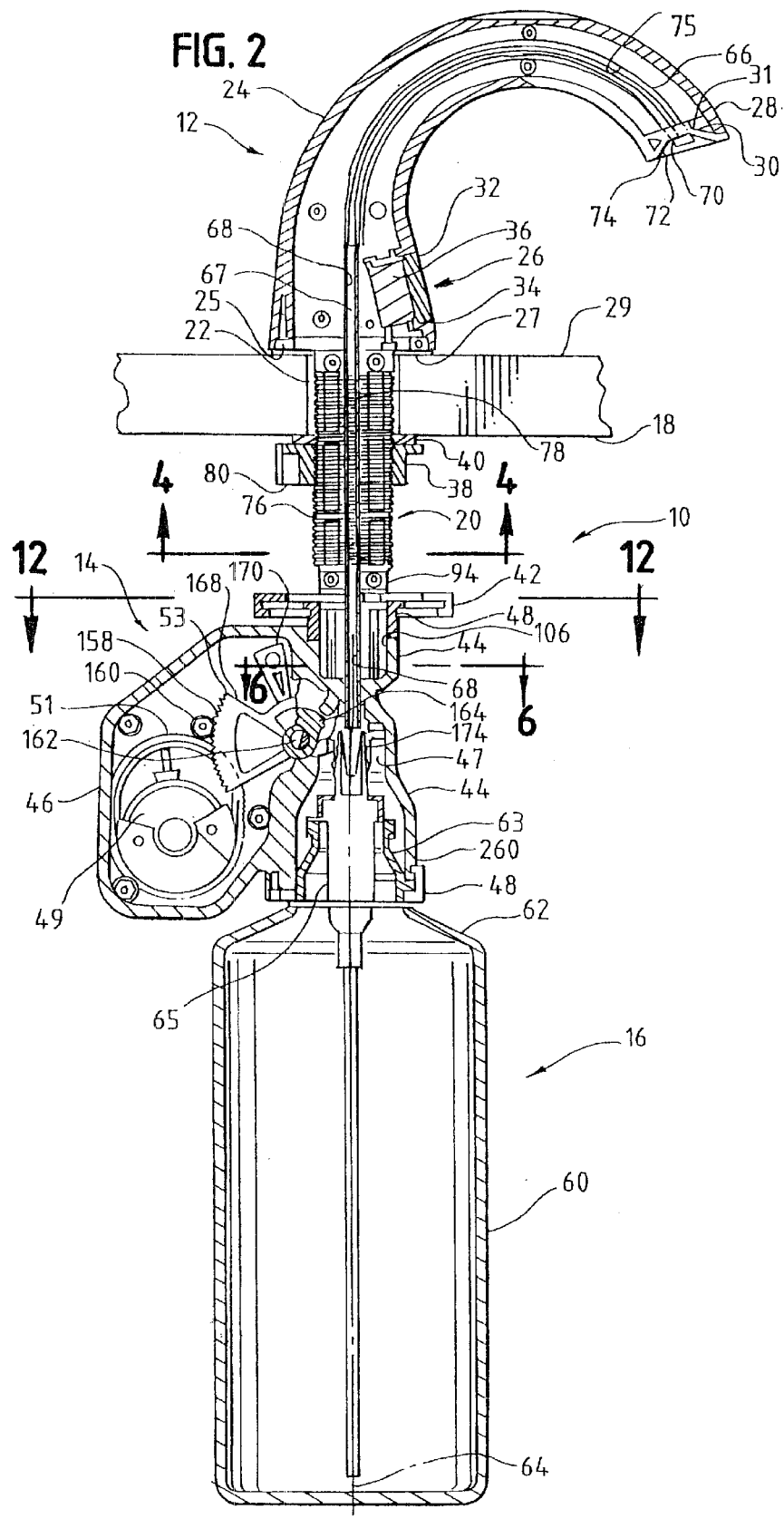
FIG. 2 is a sectional elevation view of the automatic soap dispenser of FIG. 1, taken along line 2—2.
Figure 31:
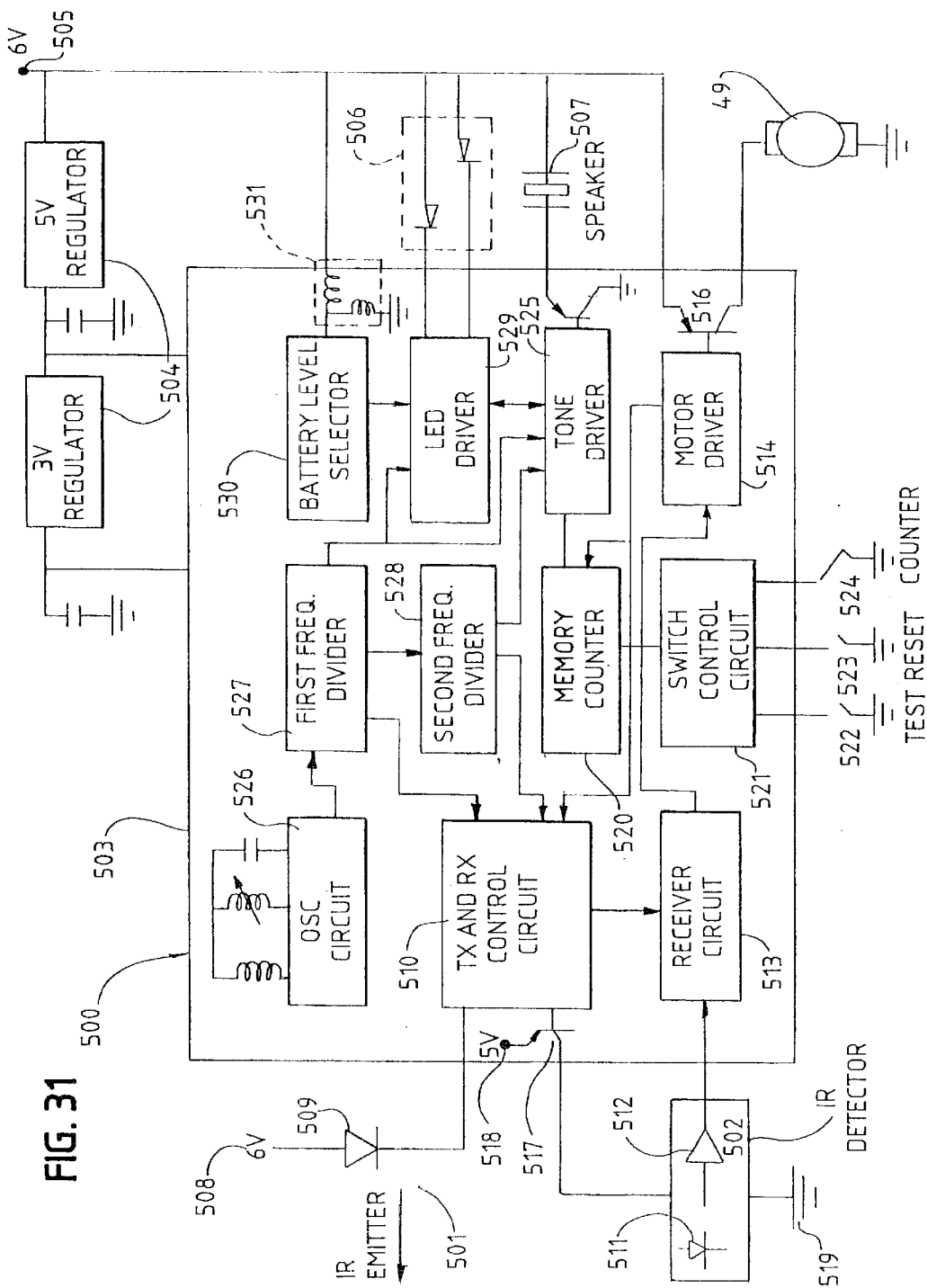
FIG. 31 is a schematic diagram of an embodiment of the circuit controlling the operation of the automatic soap dispenser of the invention.

As may be seen in FIG. 2, motor and actuator mechanism housing 46 may include a motor 49, gear reduction train 51 and pump hammer 53. The operation of pump hammer 53 is described in detail with reference to FIGS. 2 and 15A, B, C. A switch control circuit 521 of FIG. 31 may control the operation of motor 49. A connector wire 50 (FIG. 1 and FIG. 4) electrically connects the electric eye assembly 36 in housing portion 26 (FIG. 1 and FIG. 29) to the switch control circuit 521 (FIG. 31).

As seen in FIG. 1, fluid dispensing system 10 may also include a detached battery pack 52. The battery pack 52 is electrically connected to motor and actuator mechanism housing 46 through wire 54 and wire 56. Attachment element 58 allows wire 54 to be removably connected to wire 56 during installation of automatic fluid dispensing system 10. In an alternate embodiment (not shown), battery pack 52 may be permanently or removably attached to motor and actuator mechanism housing 46. In the illustrated embodiment, battery pack 52 holds a power supply to drive motor 49 and operate the electronic components of electric eye assembly 36.

The lower portion or end 260 of pump housing 44 may include structure that contributes to releasably holding fluid soap reservoir container 60 to motor housing and support assembly 14. Container 60 includes a top closure 62 having an opening 63 therein through which pump mechanism 65 extends (FIG. 2). In the illustrated embodiment, container 60 is cylindrically shaped around a central axis 64. Opening 63 in container 60 is also centered around axis 64. Axis 64 may be thought of as a longitudinal axis. As will be explained, mounting clip 48 is adapted to releasably and securely hold container 60 to pump housing 44.

FIG. 2, is a sectional vertical view of the automatic soap dispenser taken off of line 2—2 of FIG. 1. As seen, the rigid spout 24 may include a curved internal passageway 66 that extends from base 25 through the spout 24 to connect with the spout opening 31. When reservoir module and pump assembly 16 is attached to motor housing and support assembly 14, as shown in FIG. 2, a tube end 70 of elongated dispensing tube 68 will move reciprocally in passageway 66 upon actuation of pump mechanism 65. Indented outlet 30 may include an indented portion 72 that is set back from a spout tip 74 of spout 24. The indented portion 72 may provide a shield around the tube end 70 of dispensing tube 68. The indented portion 72 may prevent the tube end 70 from being viewed by a user when the tube end 70 of the dispensing tube 68 extends beyond the spout opening 31.

Electronic eye housing portion 26 of spout 24 is located above base portion 25. As may be seen in FIG. 5, tube end 70 may define an axis that forms an angle 71 with a line that is parallel to axis 67 as axis 67 passes through support shaft 20. Moreover, opening 32 of housing portion 26 may define an axis that extends in a direction facing an axis of the spout opening 31 to form an angle 73. As will be explained, the individual sensors infrared (IR) emitter 501 and IR detector 502 (FIG. 31) may be included as part of electric eye sensor 36 to detect the presence of a user's hands beneath the spout opening 31, and, in response, to activate a switch to initiate operation of fluid dispensing system 10, as will be explained.

The surface 75 of internal passageway 66 is composed of a smooth material to provide a substantially frictionless path for movement of elongated dispensing tube 68 in passageway 66 during installation and removal of reservoir module and pump assembly 14 and during each actuation of the fluid dispensing system 10. In addition, the radius of curvature of internal passage 66 is configured to allow elongated dispensing tube 68 to slidably and smoothly move inside passage 66. By way of example, in the illustrated embodiment, the radius of curvature of passageway 66 is approximately two inches. Dispensing tube 68 is made of LDPE (low density polyethylene), or other suitable material which will not react with the chemicals in the soap, and which provides a smooth outer surface to accommodate almost frictionless movement of tube 68 in passageway 66.

Passageway 66 is centrally disposed in spout 24 throughout the length of the passageway 66 to define axis 67. As seen in FIG. 2, the axis 67 of the lower end of passageway 66 is aligned at one end with central axis 64 of container 60. Thus, when elongated tube 68 and container 60 are rotated during installation of a full container 60, as will be explained, tube 68 rotates in passageway 66 about central axis 67 throughout the length of passageway 66. Since tube 68 is centrally located about axis 64, and is centrally located in passageway 66, container 60 is able to be rotated to be properly positioned relative to pump housing 44 during installation and removal of container 60.

Figure 3:
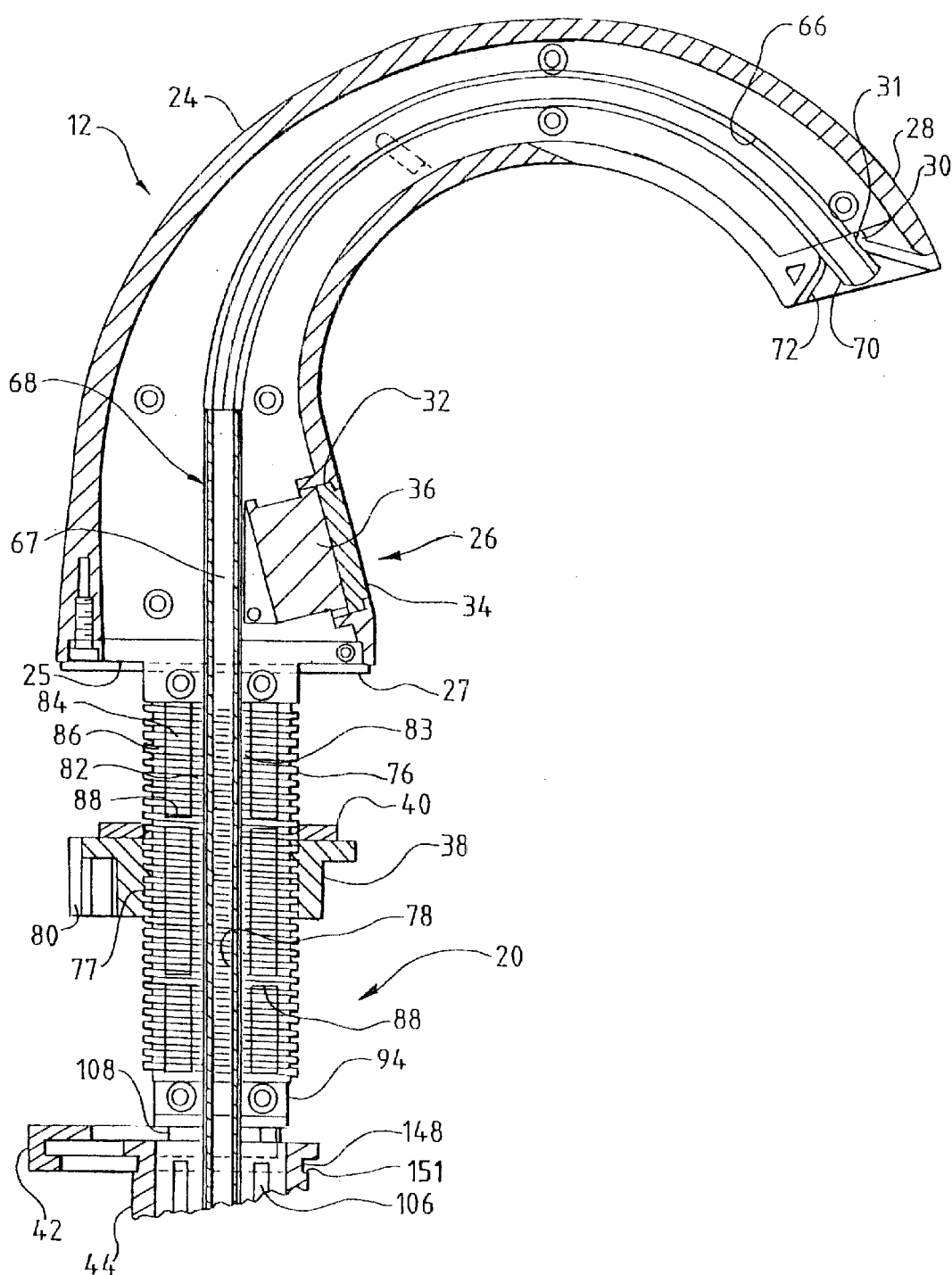
FIG. 3 is an enlarged detail sectional view of the rigid spout and threaded shank portion of the automatic soap dispenser of FIGS. 1 and 2.

As seen in FIGS. 2 and 3, support shaft 20 has external threads 76, and an internal passageway 78 through which elongated dispensing tube 68 extends. Nut 38 includes mating internal threads 77 which engage external threads 76, permitting nut 38 to be rotated and moved upward to engage the underside 33 of countertop 18 and secure support shaft 20 and spout 24 against movement relative to the countertop 18. Nut 38 is provided with outwardly extending finger grips 80 to provide facile rotation of nut 38 during installation of fluid dispensing system 10.

Referring to FIGS. 3 and 4, passageway 78 includes walls 82 and 83 formed inside the hollow portion 84 of support shaft 20. Walls 82 and 83 are held in place at a distance from outer wall 86 of support shaft 20 through ribs 88. External threads 76 are formed in outer wall 86 substantially along the length of support shaft 20. Hollow portion 84 of support shaft 20 also includes a channel 90 (FIG. 4) extending the length of support shaft 20 as a path to route the connector wire 50 from electric eye sensor 36 to a clip (not shown) on a distal or lower end of wire 50. The lower end of wire 50 extends from an opening 92 (FIG. 1) in a lower portion 94 of support shaft 20 beneath external threads 76. Passageway 78 is also formed by the end 96 of prong 98. Prong 98 extends the length of support shaft 20 between walls 82 and 83. End 96 of prong 98 is adapted to engage the outer surface of dispensing tube 68 when tube 68 is inserted into or removed from passageway 78, when dispensing tube 68 rotates in passageway 78, and when tube 68 moves reciprocally in passageway 78 in response to the actuation of the pump mechanism 65.

Figure 6:
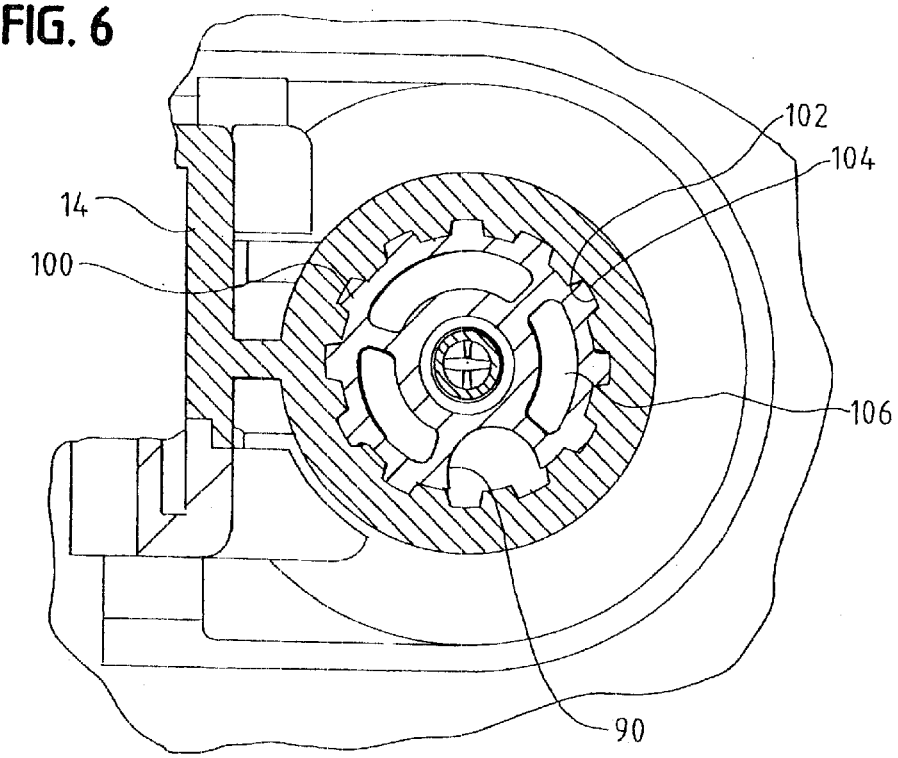
FIG. 6 is a cross-sectional view of the connection between the support shaft and the motor housing and support assembly, taken along line 6—6 in FIG. 2.

Referring to FIG. 5, extending from the lower portion 94 of support shaft 20 is a cylindrical attachment shaft 100. Attachment shaft 100 may include a plurality of circumferentially disposed splines 102. In the illustrated embodiment, splines 102 are disposed at thirty degree intervals, for reasons to be explained. Motor housing and support assembly 14 of FIG. 6 may include a plurality of grooves 104 circumferentially disposed in the interior portion 106 of motor housing and support assembly 14. Splines 102 are adapted to mate with the plurality of grooves 104 to provide for the attachment of motor housing and support assembly 14 to support shaft 20. This arrangement may permit the internal passageway 78 of support shaft 20 to align with the central interior portion 106 of motor housing and support assembly 14.

A unique assembly structure including shank clip 42 provides easy attachment and detachment of motor housing and support assembly 14 to support shaft 20. As seen in FIGS. 3 and 5, the lower portion 94 of support shaft 20 includes a shaft groove 108. The shaft groove 108 may be a circumferentially indented groove and include a bottom 109. Shank clip 42 (FIGS. 1, 2, 8–11) is adapted to secure motor housing and support assembly 14 to support shaft 20.

Figure 9:
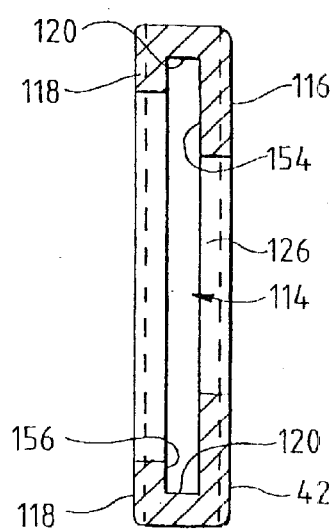
FIG. 9 is a cross-sectional view of the clip of FIG. 8, taken along line 9—9.
Figure 10:
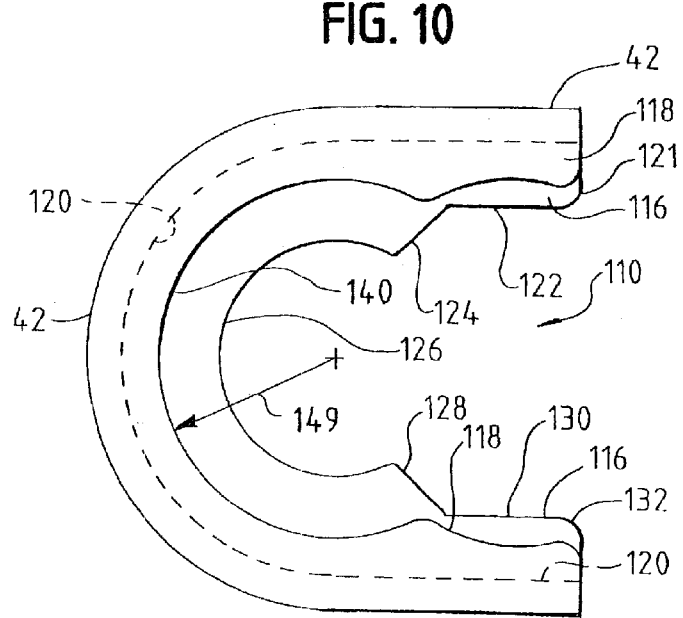
FIG. 10 is a bottom plan detail view of the clip of FIG. 8.
Figure 11:
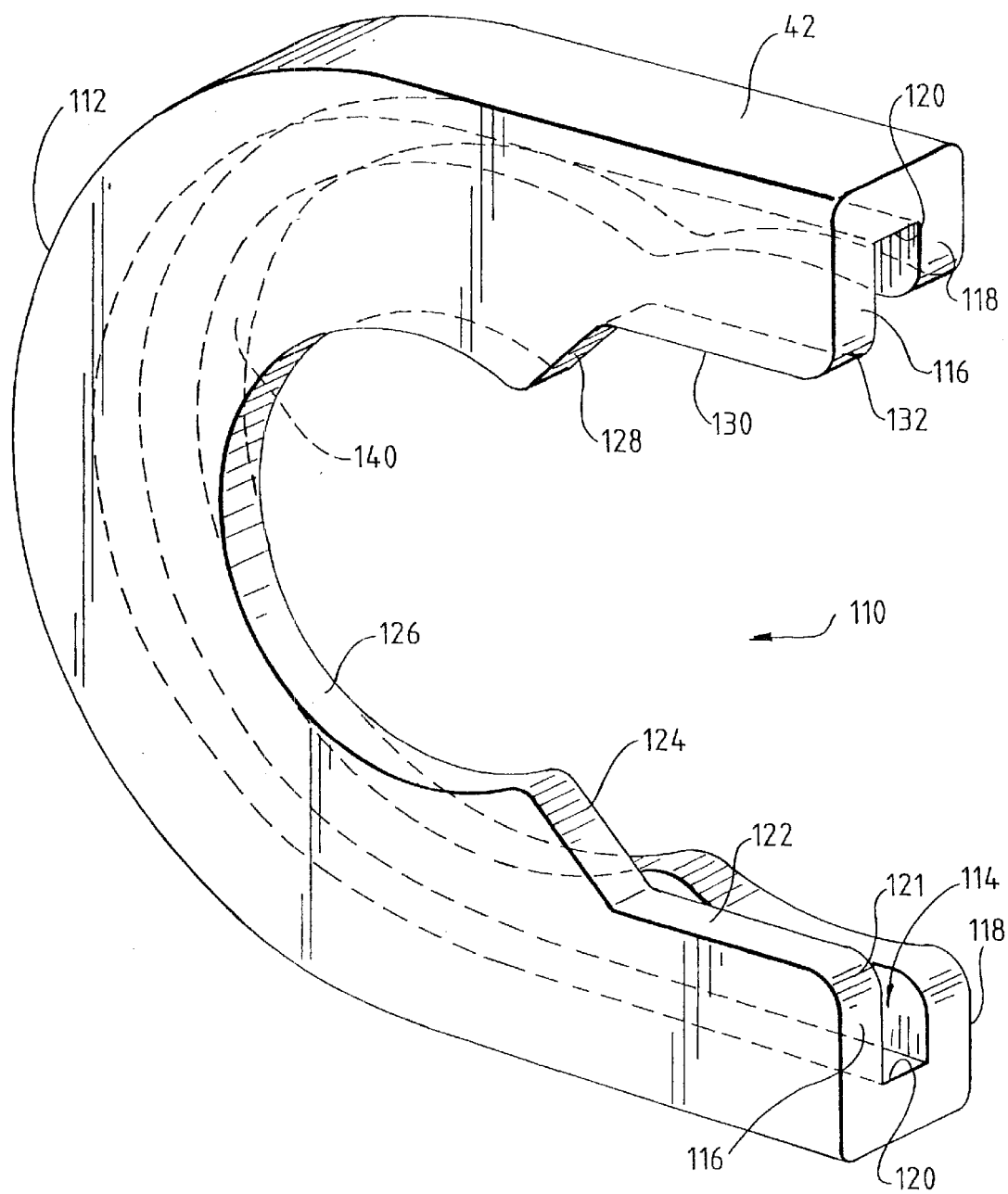
FIG. 11 is a perspective view of the clip of FIG. 8.

FIGS. 8–11 illustrate a top, side, bottom, and isometric view of shank clip 11. Shank clip 42 is generally U-shaped, having an opening 110 and a curved closed end 112. As seen in FIGS. 9 and 11, shank clip 42 provides a channel 114 that follows an interior path about the U-shaped length of shank clip 42. Along with resilient bottom 120, resilient sidewall 116 and sidewall 118 define channel 114. As illustrated in FIGS. 8–11, sidewall 116 has a generally greater height than sidewall 118 around the length of U-shaped shank clip 42 and each sidewall 116 and sidewall 118 defines a specific contour to enable the shank clip 42 to provide a removable snap fit to engage and hold motor housing and support assembly 14 to support shaft 20.

Each inwardly facing portion of sidewall 116 includes a curved first entry radius 121, a generally flat first portion 122 and a generally flat second portion 124 having a first end intersecting first portion 122 at an angle 123. A second end of second portion 124 is connected to a substantially circular portion 126. Circular portion 126 extends beyond 180 degrees by an angle 125. In one embodiment, angle 125 is thirty degrees so that circular portion 126 extends to approximately 240 degrees to the opposite side of shank clip 42. Circular portion 126 may extend to connect to a generally flat third portion 128. Third portion 128 intersects a generally flat fourth portion 130. At the end of fourth flat portion 130 is a curved second entry radius 132.

Each inwardly facing portion of sidewall 118 of shank clip 42 includes an entry radius 134, to which is connected a curved first portion 136 terminating in a first nub 138. The nub 138 is connected to a substantially circular portion 140 which extends beyond 180 degrees by the angle 125. In one embodiment, angle 125 is thirty degrees so that circular portion 140 extends to approximately 240 degrees to the opposite side of shank clip 42. Circular portion 140 is connected to a second nub 142, which connects to curved portion 144 of sidewall 118. An entry radius 146 is provided at the outer end of sidewall 118.

As may be seen in FIGS. 8–11, in the illustrated embodiment, the dimensions and configuration of the inwardly facing surfaces forming the tops of sidewall 116 are different from the dimensions and configuration of the inwardly facing surfaces forming the tops of sidewall 118. By way of example and not of limitation, in the illustrated embodiment the radius 147 of circular portion 126 of sidewall 116 is approximately 0.327 inches, and the radius 149 of the circular portion 140 of sidewall 118 is approximately 0.502 inches. The shank clip 42 is composed of rigid but flexible material, such that the shank clip 42 is strong enough to hold motor housing and support assembly 14 together with support shaft 20 while having sufficient flex in the lateral direction to allow two snap action positions to function properly, as explained below.

Subsequent to mounting spout 24 and support shaft 20 to countertop 18 (FIGS. 1, 2), the grooves 106 of the upper interior portion 106 (FIG. 6 and FIG. 7) of motor housing and support assembly 14 is moved upwardly into engagement with the splines 102 of the cylindrical attachment shaft 100 of support shaft 20 until splines 102 mate with grooves 104.

As best seen in FIG. 3, a pump housing groove 148 circumscribes the outer, upper surface of pump housing 44. Pump housing groove 148 may include bottom 151 and be adapted to receive in a first position shown in FIG. 12A, the curved portion 136 and curved portion 144 of the sidewall 118 of the shank clip 42 (FIG. 10) through opening 110 of shank clip 42. Pump housing groove.148 further may be adapted to receive in a second position shown in FIG. 12B, circular portion 140 of the sidewall 118 through opening 110.

Figure 12A:
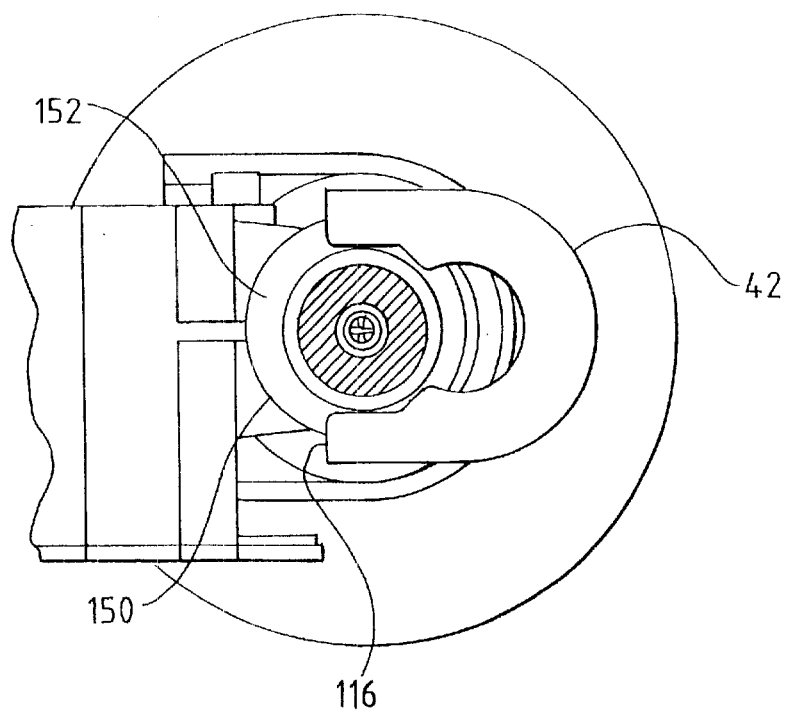
FIG. 12A is a sectional view of the support shaft and motor housing and support assembly taken along line 12—12 of FIG. 2, showing the locking clip in its unlocked position.

Prior to moving motor housing and support assembly 14 into contact with attachment shaft 100, shank clip 42 is manually and partially mounted on assembly 14 by inserting sidewall 118 into engagement with pump housing groove 148. In this first position, complementary entry radius portions 134 and 146 are urged about pump housing groove 148. This may cause shank clip 42 to flex outward and then back inward. On shank clip 42 flexing inward, curved portions 136, 144 engage the bottom 151 of pump housing groove 148. The dimensions of curved portions 136, 144 and the shank clip 42 as well as the inherent flexibility of shank clip 42 may cause the shank clip 42 to be somewhat firmly mounted in this first position on the outer upper surface of pump housing 14. This retains the shank clip 42 against the pump housing groove 148 as seen in FIG. 12A. With the shank clip 42 retained against the pump housing groove 148 may free the user to use both hands to bring the motor housing and support assembly 14 into engagement with attachment shaft 100.

Upon moving motor housing and support assembly 14 into engagement with attachment shaft 100, the circumferential distance between adjacent splines 102 and grooves 104 allows the motor housing and support assembly 14 to be rotated in thirty degree increments, allowing placement of the motor housing and support assembly 14 to avoid interfering with the underside of the sink bowl and other plumbing or structural elements located under countertop 18. This also allows the assembly 14 to be positioned for ease of access in case a need to service the fluid dispensing system 10 arises.

Figure 12B:
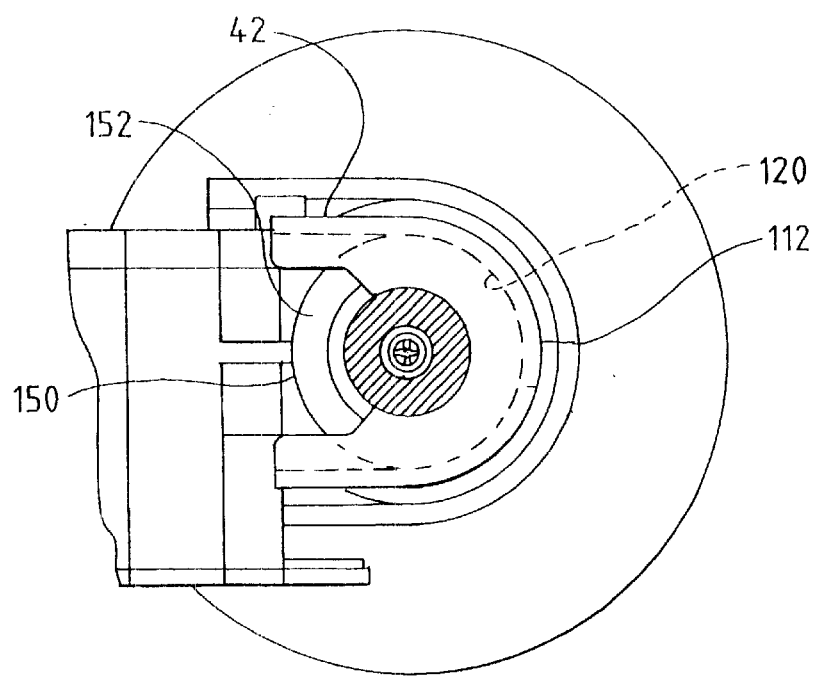
FIG. 12B is a sectional view of the support shaft and motor housing and support assembly taken along line 12—12 of FIG. 2, showing the locking clip in its locked position.

After motor housing and support assembly 14 is positioned and installed on attachment shaft 100, the shank clip 42 is manually moved laterally inward from its first position (FIG. 12A) to a second position (FIG. 12B). To reach this second position, the sidewalls 116, 118 flex slightly outward and then inward to permit circular portion 140 of shank clip 42 to engage the bottom 151 of pump housing groove 148 over the full extent of circular portion 140 and to permit circular portion 126 of shank clip 42 to engage the bottom 109 of shaft groove 108 (FIG. 5) of support shaft 20. In the illustrated embodiment of FIGS. 8–11, circular portion 140 extends 240 degrees around the bottom 151 of pump housing groove 148 and circular portion 126 extends 240 degrees around the bottom 109 of shaft groove 108, each secured to the other by the shank clip 42 as shank clip 42 removably resides in its second position.

Figure 7:
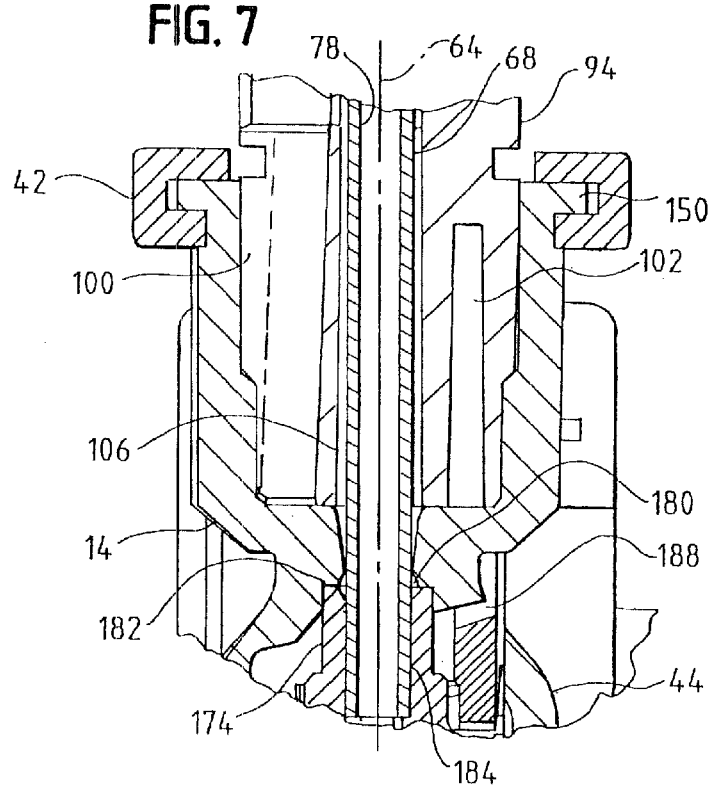
FIG. 7 is a detail section view of the splined connection between the support shaft and motor housing and support assembly of the invention.
Figure 8:
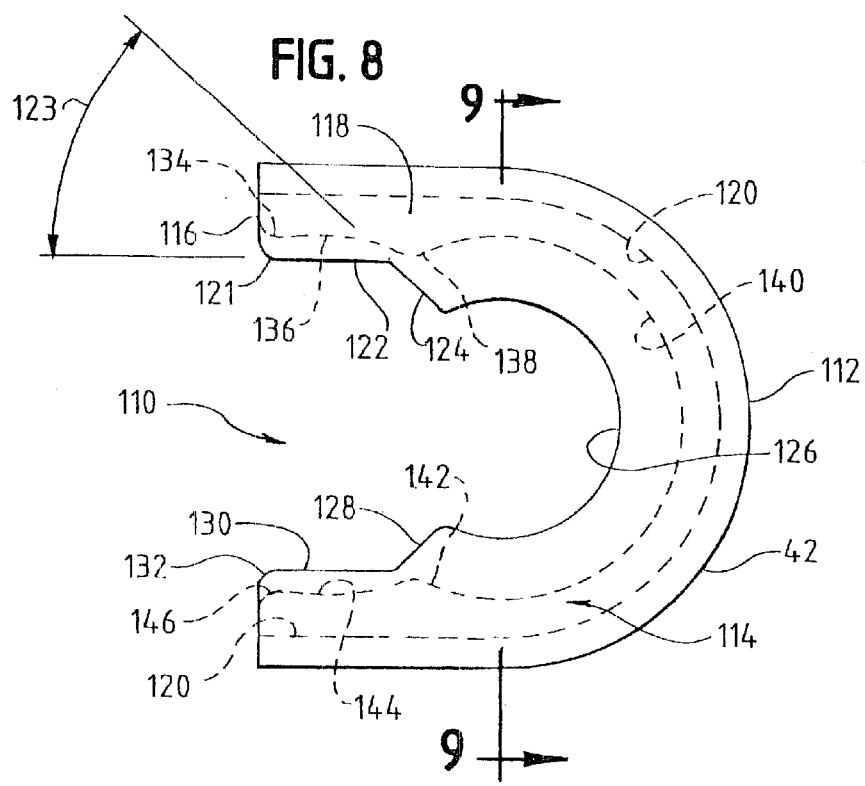
FIG. 8 is a top plan detail view of the clip adapted to removably connect the motor housing and support assembly to the support shaft of the invention;.

As best viewed in FIG. 3 and FIG. 7, pump housing groove 148 in motor housing and support assembly 14 is partially formed by a flange 150. Flange 150 may include an upward facing surface 152. As shank clip 42 is moved inward towards axis 67, the surface 154 of shank clip 42 (FIG. 9) slides across a portion of upper surface 152 of flange 150. Moreover, the surface 156 slides across a portion of the underside of flange 150. This works to slidably engage flange 150 within the channel 114 of shank clip 42 (FIG. 9). As shank clip 42 is advanced inwardly further towards axis 67, sidewall 118 moves into pump housing groove 148 as described above, and sidewall 116 moves into now adjacent shaft groove 108 of support shaft 20 (FIG. 12B), until flat portions 124, 128 (FIG. 12A) contact the bottom 109 of shaft groove 108. The shank clip 42 then flexes outward and then inward to allow circular portion 126 of sidewall 116 to engage the top of shaft groove 108 around shaft groove 108 (FIG. 12B) over a radian distance of 180 degrees plus two times the value of angle 123. In the illustrated embodiment, circular portion 126 of sidewall 116 extends approximately 240 degrees around shaft groove 108, although this dimension may vary. With shank clip 42 in its position shown in FIG. 12B, flange 150 is firmly engaged between surfaces 154 and 156 of sidewalls 116, 118 respectively. Additionally, circular portion 126 of sidewall 116 firmly engages the bottom 109 of the shaft groove 108 and circular portion 140 firmly engages the bottom 151 of pump housing, each with a snap action. Thus, motor housing and support assembly 14 is removably and firmly held to support shaft 20, until shank clip 42 is manually moved outwardly to disengage the shank clip 42 from at least shaft groove 108.

As noted above, motor housing and support assembly 14 includes pump housing 44 and motor and actuator mechanism housing 46. When motor housing and support assembly 14 is installed on support shaft 20 as described above, assembly 14 provides the driving force for the operation of pump mechanism 65. Referring to FIG. 2, motor 49 is mounted in housing 46 and is electrically connected to electric eye sensor 36 through connecting wire 50 (FIG. 1). Motor 49 also may be electrically connected to a source of power contained in battery pack 52 through wires 54, 56 and connector 58. Electric eye sensor 36 acts as a switch to toggle motor 49 between on and off, or if desired, sensor 36 could trigger operation of a separate switch (not shown) to activate motor 49.

Figure 13:
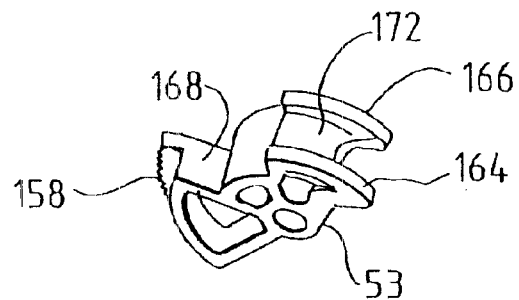
FIG. 13 is a detail perspective view of the pump hammer of the invention.
Figure 15A:
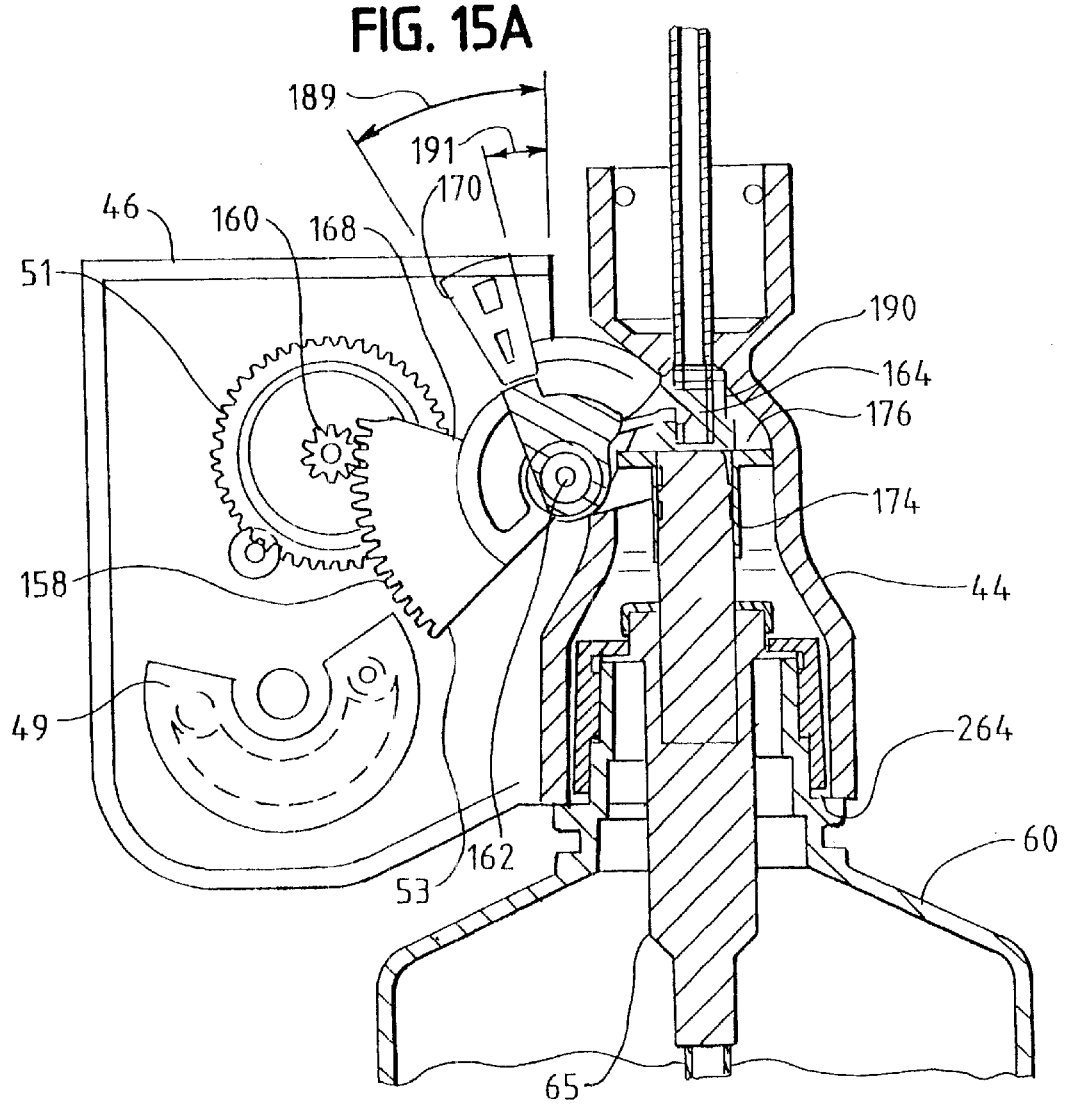
FIGS. 15A, 15B and 15C are detail schematic views showing the phases of operation of the pump hammer against the pump actuator flange upon actuation of the pump hammer of the invention.

A gear reduction train 51 mounted for rotation in housing 46 operatively connects the output of motor 49 to pump hammer 53. Pump hammer 53 is illustrated in detail in FIG. 13. Referring to FIG. 2 and to FIG. 13, the pump hammer 53 includes an actuate gear portion 158 which meshes with spur gear 160, which in turn is driven by motor 49 through gear reduction train 5 1. Pump hammer 53 is mounted on pin 162 for rotation through a small arc relative to housing 46. At an end of pump hammer 53 in the illustrated embodiment of FIG. 13 may be a pair of actuator arms 164, 166 which rotate as pump hammer 53 rotates through a small arc. Pump hammer 53 also includes a flat face 168 adapted to engage hammer kick back stop 170 (FIG. 15A). The hammer kick back stop 170 may be rigidly, but adjustably, mounted on the interior of housing 46, as seen in FIGS. 1, 12 2 and 15A–C. Optionally, hammer kick back stop 170 may be adjustably mounted on housing 46. As may be seen in FIG. 13, the space between actuator arms 164, 166 defines an open space 172.

Figure 14:
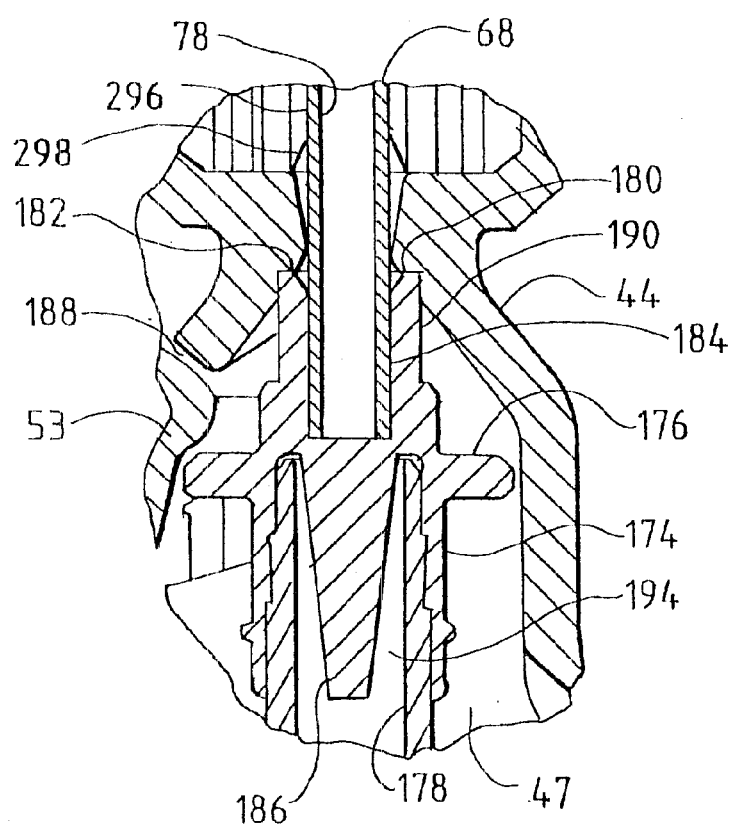
FIG. 14 is a detail elevation section view of the pump actuator of the invention, shown positioned in the pump housing.

Reference now will be made to hollow interior 47 (FIG. 2 and FIG. 14) of pump housing 44. Disposed in the hollow interior 47 of pump housing 44 is a pump actuator 174. Pump actuator 174 may be thought of as a pump mechanism actuator and may include an actuator flange 176 extending outward from and circumscribing the body of actuator 174. As seen in FIG. 14, pump actuator 174 engages hollow pump intake tube 178 connected to pump mechanism 65 (FIG. 2), and moves downward when pump mechanism 65 is actuated, as will be explained in further detail. The upper movement of actuator 174 is limited by the abutment of top surface 180 of the actuator against inwardly directed limiting surface 182 of pump housing 44, as seen in FIG. 14.

Elongated dispensing tube 68 is firmly lodged in cylindrical opening 184 of actuator 174, whereby dispensing tube 68 moves in reciprocal directions within passageway 78 along with the movement of actuator 174. Actuator 174 also includes a downwardly extending member 186 adapted to allow passage of fluid soap from the reservoir container 60 through the actuator 174 and into dispensing tube 68, as will be explained in further detail. As shown in FIG. 14, pump housing 44 is provided with an opening 188 in one sidewall to allow selective contact between pump hammer 53 and flange 176 of actuator 174.

FIG. 15A illustrates the condition of pump hammer 53 when the motor 49 is not energized. Here, pump hammer 53 is in its full kick back position. Actuator arms 164, 166 (hidden) straddle upper portion 190 of actuator 174, such that upper portion 190 extends into open space 172 (FIG. 13) as pump hammer 53 pivots clockwise around pivot pin 162 under the influence of motor 49. In FIG. 15A, actuator arms 164, 166 are disposed a short distance above opposite lateral sides of the upper surface of actuator flange 176.

Figure 15B:
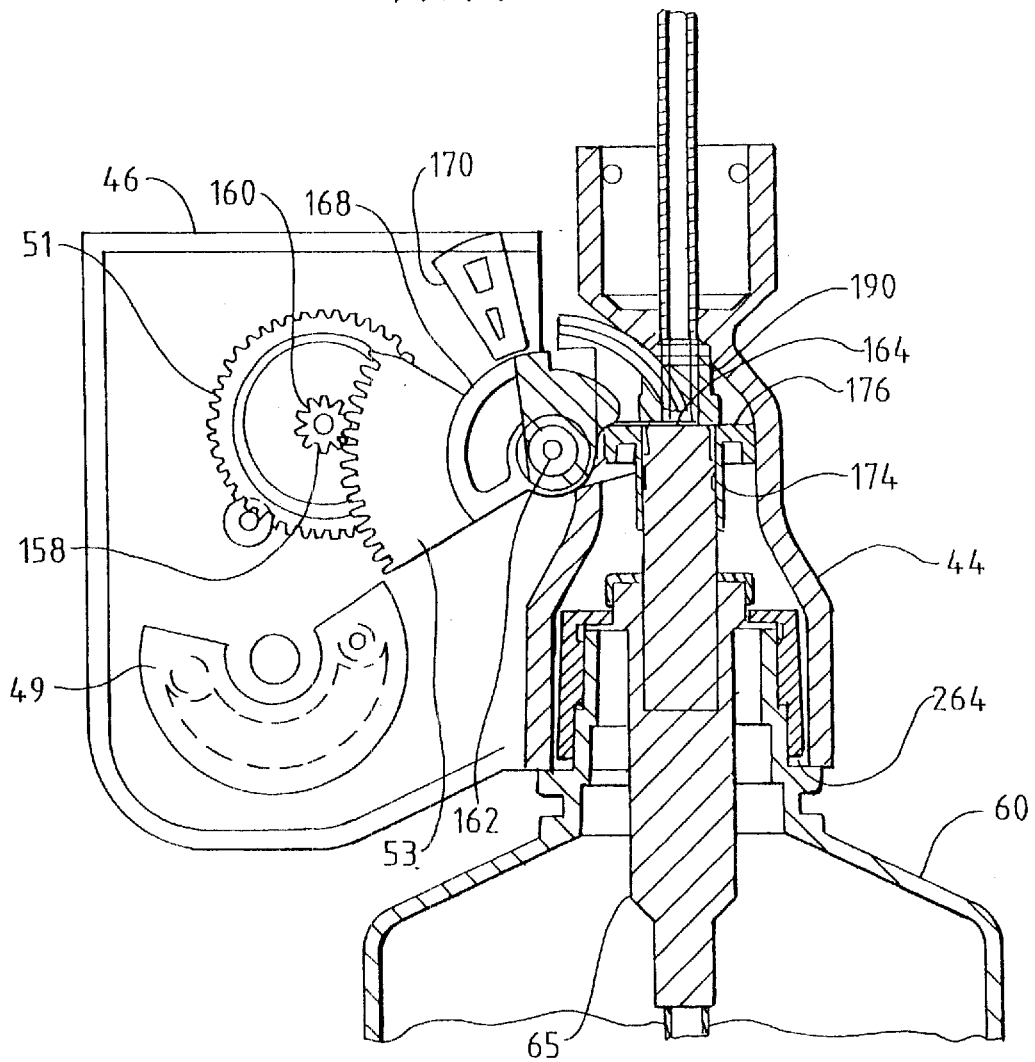
Figure 15C:
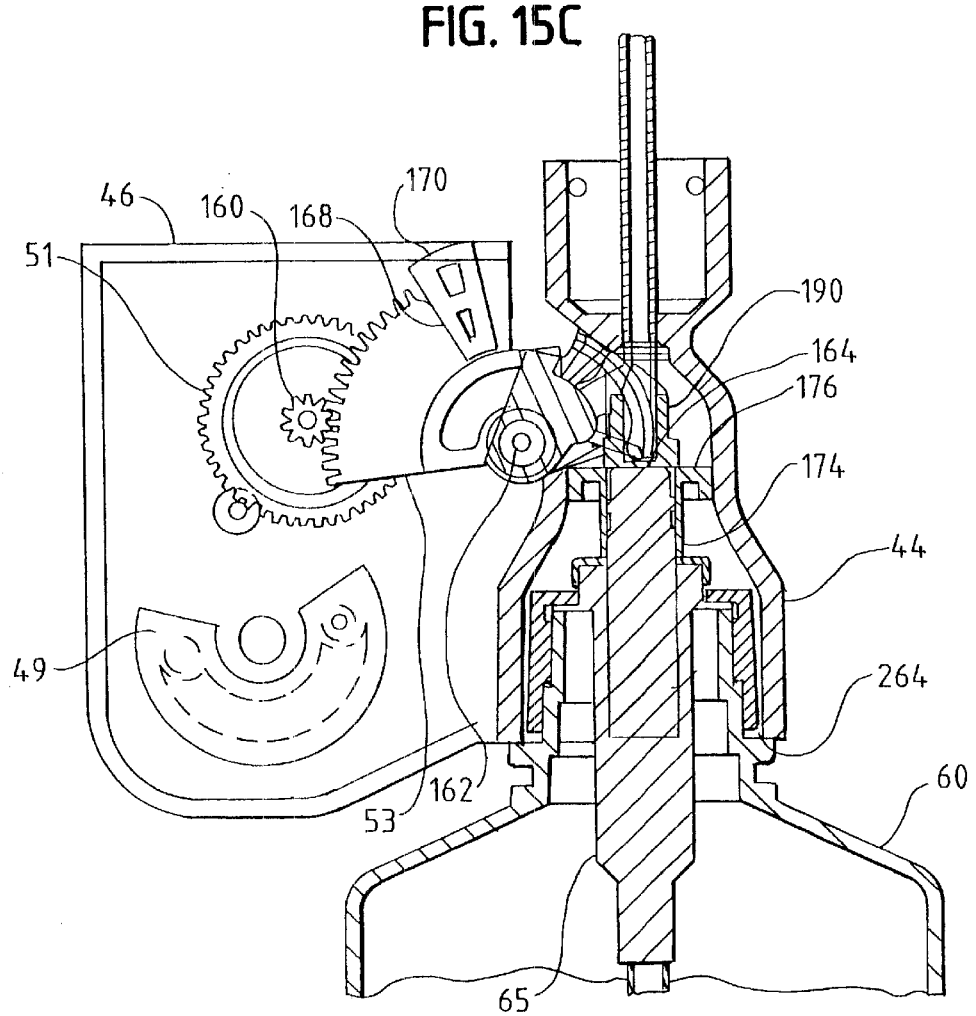

Upon actuation of motor 49, gear reduction train 51 drives spur gear 160 which, in turn, drives pump hammer 53 clockwise, as viewed in FIG. 15B, until the outer ends of actuator arms 164, 166 initially engage opposing upper surface locations on actuator flange 176. At this point, motor 49 continues to operate, rotating pump hammer 53 further clockwise, and advancing pump actuator 174 downward into pump mechanism 65, as shown in FIG. 15C.

The amount of downward movement of pump actuator 174 determines the amount of fluid soap that is dispensed from elongated tube 68 at tube end 70 upon each actuation of automatic soap dispenser 10. The distance of the downward movement of pump actuator is controlled by the position of hammer kick back stop 170. The position of hammer kick back stop 170 may be defined by angle 189 as measured from the center of pin 162 to a distal surface of stop 170. In one embodiment, angle 189 is thirty one degrees. Angle 191 references a storage position of actuator arms 164, 166 and may be measured from the center of pin 162 to a local surface of stop 170. In one embodiment, angle 191 is thirteen degrees. To dispense a desired dosage of the fluid soap, flat face 168 of pump hammer 53 abuts kick back stop 170, thus halting further clockwise rotation of pump hammer 53.

Referring to FIGS. 15A, B and C, when flat face 168 of pump hammer 53 abuts hammer kick back stop 170, the motor 49 stalls and the current through the motor 49 increases. The increase in current through the stalled motor 49 is detected by the circuitry (FIG. 31), and the drive 514 to the motor 49 ceases, thus preventing the delivery of torque by the motor 49 to pump hammer 53. With the motor 49 off, the spring 236 in pump mechanism 65 (FIG. 20) causes the pump chamber 218 to expand, whereby flange 176 of pump actuator 174 moves upward to force pump hammer 53 to rotate counterclockwise back to its start position. Inertia from gear reduction train 51 carries the counterclockwise rotating pump hammer 53 to the position shown in FIG. 15A.

Figure 16:
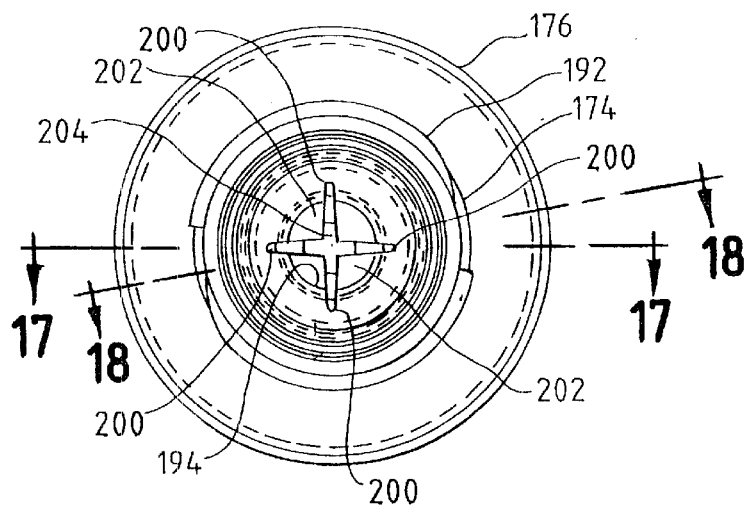
FIG. 16 is a cross-sectional view of the pump actuator of the invention, taken along line 16—16 in FIG. 17.
Figure 17:
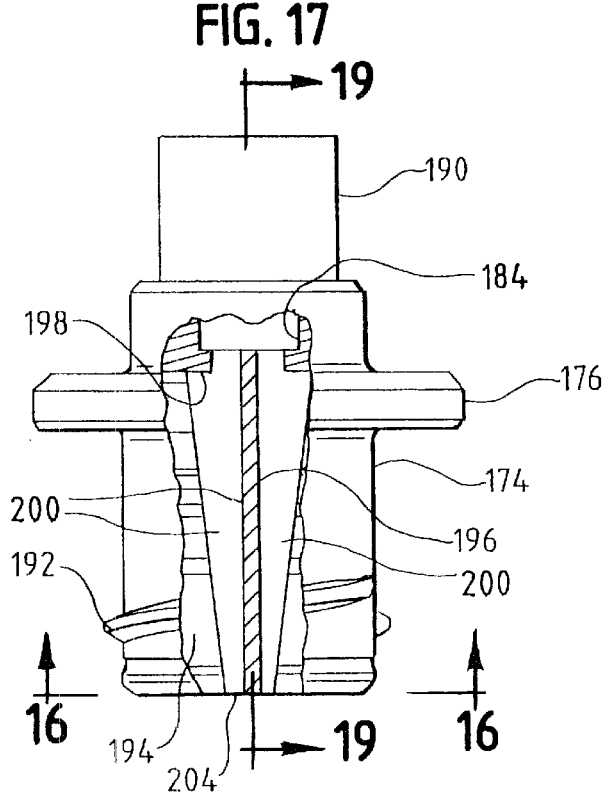
FIG. 17 is an elevation, partial section view taken along line 17—17 of FIG. 16.

FIGS. 16 and 17 are detail views of the pump actuator 174, showing a beveled form of actuator flange 176, which operates the same as the previously described embodiment. The external body of actuator 174 includes a single circumscribing thread 192, which is adapted to mate with corresponding internal threads 258 (FIG. 20) in the neck of container 60 to hold actuator 174 and intake tube 178 in an inoperative position during shipment of reservoir module and pump assembly 16, as will be explained.

A hollow chamber 194 (FIG. 17) is provided internally in actuator 174, and a timing shaft 196 extends downward from portion 198, where portion 198 forms the bottom of cylindrical opening 184 (FIG. 14 and FIG. 17). Recall that the dispensing tube 68 is attached to actuator 174 through cylindrical opening 184 (FIG. 14). Timing shaft 196 comprises four downwardly extending blades 200, which upper portions are attached to portion 198. Adjacent blades 200 may appear as part of a spider element to define openings 202 between blades 200 to provide for passage of fluid soap material upward along timing shaft 196, through openings 202 and into dispensing tube 68 when pump mechanism 65 is actuated. The bottom of timing shaft 196 comprises a landing 204 adapted to engage sealing upstroke ball cock 206 (FIG. 20) upon actuation of pump mechanism 65.

Figure 20:
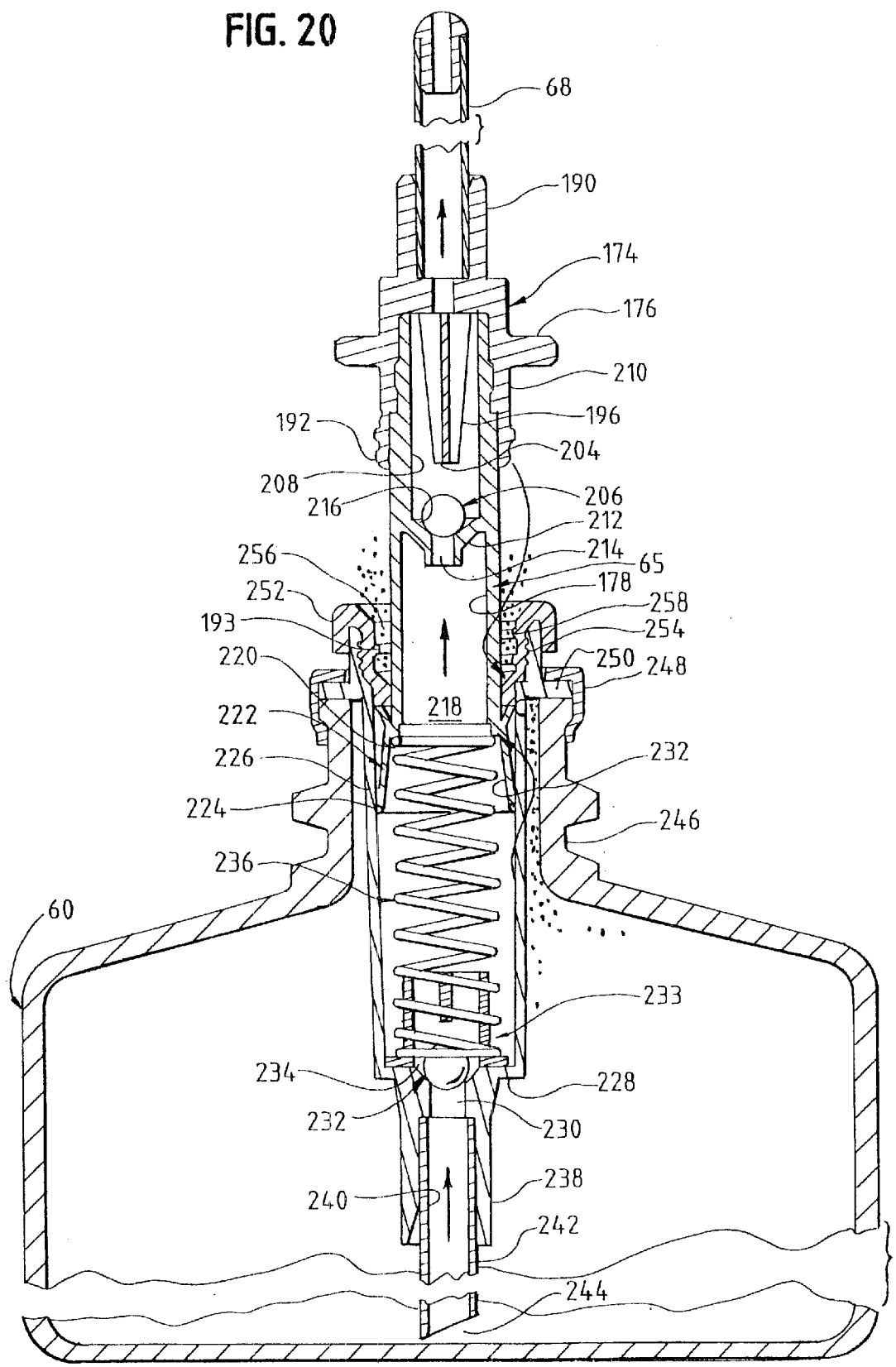
FIG. 20 is a cross-sectional schematic elevation view of the pump mechanism of the invention.
Figure 26:
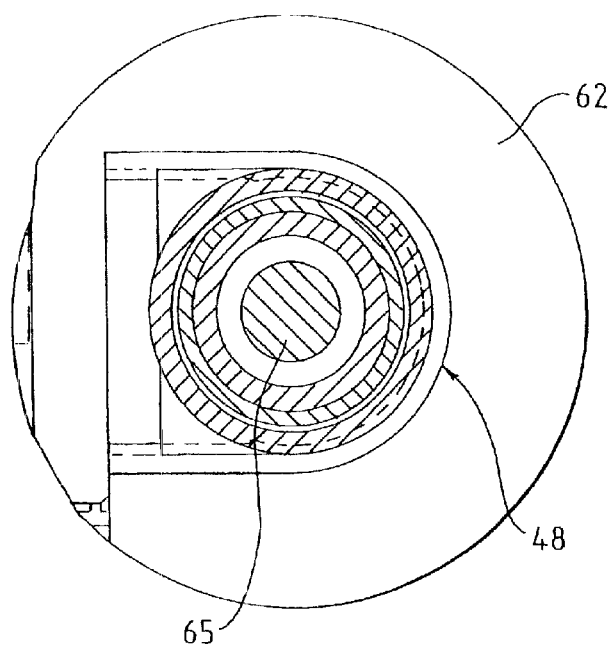
FIG. 26 is a section view of the connection between the motor housing and support assembly, and the reservoir module and pump assembly of the invention, taken along line 26—26 in FIG. 24.

FIG. 20 provides a schematic representation of the relationship between pump actuator 174, pump mechanism 65 and fluid soap container 60. For purposes of the invention, pump mechanism 65 is a standard, self priming pump as is known in the art. It is contemplated that additional pump mechanisms may be used in the invention, having structure and operation that may vary from the pump description set forth below. Pump actuator 174 sits on top of cylindrical wall 208 of intake tube 178. The actuator 174 is secured to intake tube 178 at press fit points 210. The interior of intake tube 178 includes a substantially V-shaped restriction 212 having an aperture 214 extending therethrough. Ball cock 206 is adapted to rest in the V-shaped trough 216 so as to block aperture 214 when in the rest position seen in FIG. 20.

Beneath restriction 212 in pump mechanism 65 is a cylindrical open outlet chamber 218 having a ridge 220 at the bottom thereof, and. Chamber 218 is further defined by wall 222 having outer ends 224. Wall 222 may be a resilient, outwardly extending circular wall where outer ends 224 slidably engage a stationary housing 226. Stationary housing 226 forms part of pump mechanism 65. The bottom of stationary housing 226 is defined by a circular plate 228 defining an aperture 230 centrally disposed therein. Stationary housing 226 may include a pump ball cock 232 resting in a trough 234 forming the upper portion of aperture 230. Retainer 233 sits atop circular plate 228, and forms a lower mount for spring 236. The upper end of spring 236 abuts ridge 220.

Recall that motor 49 rotates actuator arms 164, 166 to engage flange 176 so as to drive down actuator 174. Actuator 174, in turn, drives down intake tube 178. When actuator 174 drives intake tube 178 downward, spring 236 compresses and container 60 pressurizes so as to cause fluid soap to be pumped out of container 60. The spring 236 provides the force to return actuator 174 to its upward position upon stall of motor 49, as previously described.

The lower end of stationary housing 226 includes a cylindrical boss 238 having a hollow central portion 240, into which a hollow soap inlet tube 242 is inserted. Tube 242 extends downward from boss 238 to substantially the bottom of container 60, leaving a space 244 to allow soap to be conveyed from the bottom of container 60 into tube 242.

Stationary housing 226 is firmly attached to neck 246 of container 60 through a ferrule 248. Ferrule 248 is crimped both over outwardly extending flange 250 of stationary housing 226 and over neck 246. To prevent fluid soap from leaking out of container 60 during pressurized operation of pump mechanism 65 as well as during shipment of container 60, a pump sealing member 252 is firmly secured to stationary housing 226 at mating threads 254. Pump sealing member 252 is circular in configuration and has an internal chamber 256 comprising internal threads 258. Internal threads 258 are adapted to mate with single circumscribing thread 192 on pump actuator 174 during shipment of container 60. This mating may occur when intake tube 178 is moved downward against the force of spring 236 and is rotated approximately one full turn to engage internal threads 258 with actuator threads 192. This arrangement may maintain pump mechanism 65 in an inoperative position during shipping. To activate pump mechanism 65 prior to use, pump actuator 174 is counter rotated so as to disengage threads 258 and 192, a result being that intake tube 178 moves upward under the force of previously compressed spring 236.

Fluid dispensing system 10 also includes a removable fastening assembly including mounting clip 48 (FIG. 1) to enable fluid soap containers 60 to be sequentially installed on and removed from the lower end 260 of motor housing and support assembly 14. Referring to FIGS. 2 and 21–23, mounting clip 48 is securely attached to the lower end 260 of assembly 14. As may be seen in FIG. 21, mounting clip 48 includes a centrally disposed opening 262 which aligns with opening 262 (FIG. 15A) at the lower end of assembly 14. A screw, or other suitable fastener (not shown) is inserted through hole 266 (FIG. 21–23) to secure mounting clip 48 onto assembly 14.

As seen in FIG. 23, mounting clip 48 may include a lower plate 268, a wall 270 extending downward from plate 268, and an inwardly extending flange 272. In the illustrated embodiment, mounting clip 48 includes a flat rear wall 274, however the configuration of rear wall 274 may be any other suitable shape. Referring to FIGS. 21 and 23, flange 272 includes flat portions 276 on either side of opening 262, nubs 278, and circular portion 280 extending over a distance of approximately 180 degrees. The space between flange 272 and lower plate 268 defines a channel 282. Channel 282 also extends 180 degrees around opening 262, with two flat channel portions 284 extending to rear wall 274. A stop member 285 is disposed in channel 282 for purposes to be explained.

Referring to FIGS. 21–23, lower plate 268 of mounting clip 48 includes a plurality of inwardly facing protuberances 286 along the rim of opening 262 so as to define spaces 288 between the protuberances 286. Friction surfaces 290 (FIG. 21) ending in indentations 291 are provided on a surface of one or more of the upwardly facing protuberances 286. Each friction surface 290 may represent an angled thinness in a protuberance 288 that acts to wedge a protuberance 286 between a tab 292 and an upper surface 293 of container 60 when reservoir module and pump assembly 16 is installed in soap dispenser 10. Complete installation includes bumps 295 (FIG. 27) residing within indentations 291 (FIG. 21).

Figure 27:
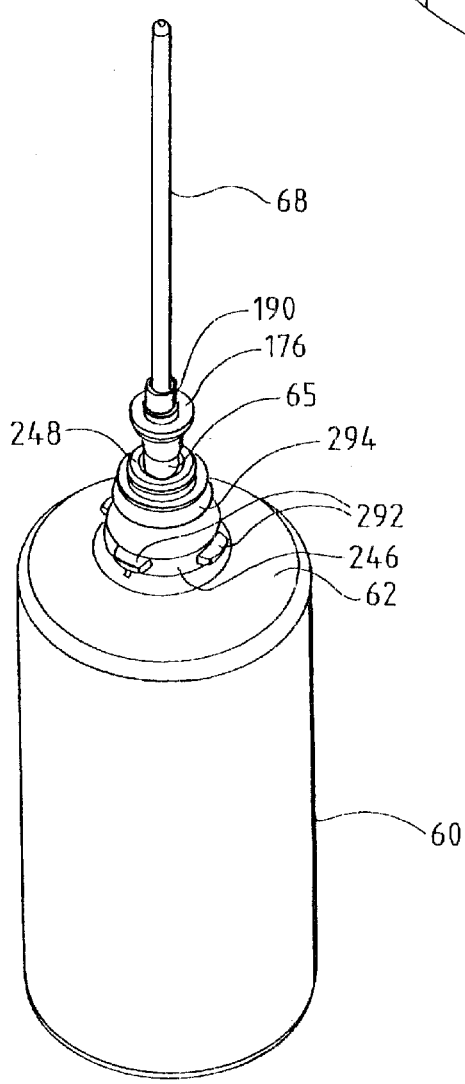
FIG. 27 is a front and top perspective view of the reservoir module and pump assembly of the invention.

Referring to FIGS. 24 and 25, mounting clip 48 is illustrated unattached to the lower end 260 (FIG. 2) of motor housing and support assembly 14 (e.g., lower end 260 is not illustrated in FIGS. 24 and 25), but it is to be understood that mounting clip 48 is to be attached to assembly 14 as shown in FIG. 2. As seen in FIG. 27, container 60 includes a neck 246, and tabs 292 where tabs 292 may extend outwardly from neck 246. Each tab 292 has a substantially flat upper and lower surface, dimensional to fit in channel 282 of mounting clip 48, as seen in FIG. 25. The illustrated embodiment of FIGS. 24–27 show four equally spaced tabs 292 located around the neck 246 of container 60. However, container 60 may contain a different tab configuration, such as three or two tabs by way of examples, if desired, with corresponding changes in number of protuberances 286 and spaces 288 in clip mounting 48 (FIGS. 21, 22).

FIG. 29 is a view of the location of electric eye sensor unit 36 in spout 24, and FIG. 31 is a block diagram view of an embodiment of the soap dispenser circuit of the fluid dispensing system 10 of the invention. In FIG. 31, the soap dispenser circuitry 500 includes an infrared (IR) emitter 501, an IR detector 502, an assembly control circuit 503, voltage regulators 504, a voltage source 505, control diodes 506 and speaker 507. In this embodiment, the IR emitter 501 is located in electric eye sensor unit 36 (FIG. 29), and includes a second voltage source 508 to provide a potential to IR emitter 501 in order to emit pulsed IR signals from the soap dispenser assembly 10. As is well known in the industry, the second voltage source 508 may be a potential creating voltage source, such as a battery or other device that creates a voltage potential to initiate a flow of electrons from the second voltage source 508. While the illustrated embodiment provides a potential of 6 V being applied to the IR emitter 501, other embodiments may vary the second voltage source 508 so long as IR signals may be pulsed from the IR emitter 501.

Also, part of the IR emitter 501 is a standard diode 509, much like control diodes 506, that controls the direction of the flow of charge from the second voltage source 508. Again, the IR emitter 501 is used to provide IR signals from the fluid dispensing system 10 as a continuous pulse, controlled by the transmission (TX) and reception (RX) control circuit 510, which is part of the assembly control circuit 503. Also outside of the assembly control circuit 503 is the IR detector 502, which is physically located in electric eye sensor unit 36 (FIG. 29). The IR detector 502 is a low current consumption device that is also controlled by the TX and RX control circuit 510. The IR detector 502 detects when an object, such as a hand upon which soap will be dispensed, is placed in the sensing field (i.e. path) of the IR signals being emitted from the IR emitter 501. The object placed in the sensing field may reflect the IR signal being emitted from the IR emitter 501 towards the IR detector 502. IR detector 502 receives the reflected IR signal and detects this IR signal. It is noted that IR signal emission is well known in the art using standard IR data transmission techniques. The IR detector 502 has, in this embodiment, a standard diode 511 to control the direction of the flow of charge and an IR detector amplifier 512. The IR detector amplifier 512 amplifies the pulsed signal and transmits that signal to the receiver circuit 513.

When three continuously received pulse signals are received by the receiver circuit 513 from the IR detector 502, the receiver circuit 513 may transmit a signal to the motor driver 514 to operate the motor 49 (FIGS. 31 and 2). It is noted that the signals being transmitted throughout the soap dispensing control circuit 503 are transmitted along standard conducting lines formed of conducting materials as is well known to those skilled in the art. Further note that the motor 49 is driven by the motor driver 514 in conjunction with the voltage source 505 and controlled by the conventional transistor 516.

In the soap dispensing circuit 503 of FIG. 31, the TX and RX control circuit 510 controls transmission of IR signals from the IR emitter 501 and reception of the reflected IR signals from the IR detector 502 that are sent to the receiver circuit 513. To control transmission of control signals between the TX and RX control circuit 510 and the IR detector 502, there is a standard transistor 517 electrically connected to a voltage source 518 (e.g., 5V). It is noted that the IR detector 502 is electrically connected to a ground 519 to properly control the flow of charge to the IR detector 502.

As previously mentioned, in one embodiment, the motor 49 is turned on (and thus soap dispenses from tube end 70 (FIG. 3)) when the receiver circuit 513 receives three (which may be more or less in other embodiments) continuous pulse signals from the IR detector 502. Three pulses allows the sensors to distinguish between an actual user, and other elements accidentally passing in front of emitter 501. When the motor 49 turns on, a signal is transmitted from the motor driver 514 to the memory counter 520, where memory counter 520 is a conventional counter well known in the industry.

In other words, the assembly control circuit 503 may include a transmission (TX) and reception (RX) control circuit 510 that is electrically connected to the IR emitter 501 and the IR detector 502 as shown in FIG. 31. The assembly control circuit 503 also may include a motor drive 514 and a receiver circuit 513 that may be electrically connected to the IR detector 502 and to the TX and RX control circuit 510. The receiver circuit 513 may be electrically connected to the motor drive 514. As explained below, the TX and RX control circuit 510 may generate a transmit signal that may prompt the IR emitter 501 to produce a pulsed IR signal. The TX and RX control circuit also may provide a bias signal to the IR detector 502 to turn on or allow the IR detector 502 to detect a pulsed IR signal. In addition, the TX and RX control circuit 510 may provide a clock signal to the receiver circuit 513 to facilitate the detection of a group of continuous pulses before dispensing soap in accordance with an exemplary implementation of the assembly control circuit 503. In one implementation of assembly control circuit 503, only when three continuously received pulse signals are received by the receiver circuit 513 from the IR detector 502 will the receiver circuit 513 transmit a signal to the motor driver 514, which in turn may operate the motor 49.

The memory counter 520 is electrically connected to a switch control circuit 521 that controls three switches, in this embodiment, including a test switch 522, a reset switch 523 and a counter switch 524. These switches 522, 523, and 524 are conventional switches that are opened and closed to provide, discharge of electrical current to ground 519, depending on which operation (e.g., testing, resetting or counting) is needed. Using the switch control circuit 521 and, in conjunction with the motor driver 514 and TX and RX control circuit 510, the memory counter 520 keeps track of the number of cycles (i.e. times soap is dispensed) and sends a signal to the tone driver 525 and light emitting diode (LED) driver 529 when a certain number of dispensing cycles have occurred (e.g., 960 or 1200 cycles) so that an indicator light 37 (FIG. 29) embedded in electric eye sensor unit 36 and visible through lens 34 (FIG. 29), or alarm (e.g., using speaker 507), may be activated to signal that the soap dispenser assembly must be refilled. Note that fluid dispensing system 10 will continue to operate after the indicator light 37 or the alarm has been activated.

Still in FIG. 31, an oscillator circuit 526, a first frequency divider 527, a second frequency divider 528, an LED driver 529, and a battery level selector 530 are all within the assembly control circuit 503. These elements provide the required signal frequency and timing for the LED driver 529 and the tone driver 525 to generate the refill indicator light and alarm signal. The oscillator circuit 526 may be electrically connected to the first frequency divider 527. The oscillator circuit 526 may produce a system frequency oscillation signal that is provided to the first frequency divider 527. The oscillator circuit 526 may include a known inductor-resistor-capacitor (LRC) circuit and logic gate inventors to produce a standard oscillation as is well known in the art. The first 527 and second 528 frequency dividers are in electrical connection with the TX and RX control circuit 510 and the tone driver 525 in order to create the required refill indicator and alarm signal.

The tone driver 525 drives the speaker 507 to provide audio sounds when the soap dispensing assembly must be refilled. Similarly, the LED driver 529, in connection with the first frequency divider 527, the battery level selector 530 and the tone driver 525, drives the indicator light 37 to signal that the soap refill is needed. Likewise, the battery level selector 530 indicates to the LED driver 529 when the batteries of the assembly must be replaced. The battery level selector is in connection with several resistors 531 that are used to control the amount of voltage arriving at the battery level selector 530. Outside of the circuit 503 are the voltage regulators 504. These regulators 504 are used to control the amount of voltage transmitted to the circuit 503 and are in electrical connection with a standard capacitor and ground to properly regulate the voltage needed by the circuit 503.

In use, the embodiment of the soap dispenser circuitry 500 of FIG. 31 continuously transmits IR signals from the IR emitter 501 outside of the soap dispensing assembly 10. When an object, such as a hand, comes within the sensing field or path of the IR signals being emitted from the IR emitter 501, the IR detector 502 receives pulses being reflected by the object and sends a signal to the receiver circuit 513. In the illustrated embodiment, when three continuous pulses have been received by the receiver circuit 513, the receiver circuit transmits a signal to the motor driver 514 which, in turn, activates the motor 49 to dispense the fluid soap. The amount of soap being dispensed is monitored by the memory counter 520, which works in conjunction with the tone driver 525 to audibly indicate through the speaker 507 or the indicator light 37 as described above when the soap must be refilled.

FIG. 32 is a flow chart of an embodiment of the method of dispensing soap of the invention. In FIG. 32, two flow charts, flow chart A and flow chart B, of the method 600 of dispensing soap are depicted. Flow chart A depicts an embodiment for a method of replacing the soap after the soap has been used by the continuous cycles depicted in flow chart B.

Flow chart A begins at step 540 by replacing the bottle container 60. Container 60 may include the soap to be dispensed through the use of the fluid dispensing system 10 of the invention. There is no requirement that the container 60 be completely full of soap, but only that some soap be present in the container 60 in order to be dispensed by the soap dispensing assembly 10. A reset button 523 (FIG 31.) is then pushed at step 541. Pushing the reset button 523 at step 541 resets the memory counter 520 of FIG. 31 to zero at step 542.

Recall that the memory counter 520 keeps track of the number of cycles (i.e. number of times soap is dispensed) and sends a signal to the tone driver 525 (FIG. 31) when a certain number of cycles have occurred (e.g., 960 or 1200 cycles) so that an indicator light 37 or alarm ( e.g., when using speaker 507 of FIG. 31) may be activated to signal that the soap dispenser must be refilled. In step 542, the counter 520 is reset since the container 60 at step 540 has been replaced with a full bottle, in one embodiment.

Still in flow chart A, at step 543, a number of priming pump actuations, for example, four, are performed in order to raise the soap from the container 40 up through the soap dispensing tube 68. Various embodiments may be used to achieve the priming pump actuations. For example, in one embodiment, the self-priming pump mechanism 65 previously described may be run four times to raise the soap from the container to the dispensing tube 68. In alternative embodiments, the dispensing tube 68 may be manually pumped by a user to raise the soap to the tube 68. Alternatively, additional pumps may be added in other embodiments to achieve the number of pumps needed to raise the soap from the container or bottle to the soap dispensing nozzle. Then at step 544, the low bottle LED 37 driven by the LED driver 529 (FIG. 31) is turned off since a new container 60 of soap has been replaced at step 540.

Flow chart B of FIG. 32 is a flow chart of an embodiment of the steps of each cycle (i.e. each time soap is dispensed) that occurs when soap is being dispensed. At step 545, the IR detector 502 (FIG. 31) which begins the soap dispensing at step 546 senses the hand of a user. Each time the soap is dispensed at step 545, a counter, for example, the memory counter 520 of FIG. 31, is incremented at step 547 in order to keep track of the amount of soap left in the container 60 or bottle. Recall that each bottle or container 60 has approximately 960 or 1200 cycles that are counted and stored so that the indicator lights 37 or alarm may alert a user or owner when the soap is running low or the container 60 is empty.

Steps 545–547 are repeated as long as the counter 520 has counted less than 900 cycles, in this embodiment which is depicted by step 548. It is noted that more or less cycles may be counted in alternative embodiments which only require larger or smaller amount of soap to be stored in the reservoir soap dispensing assembly 16. Thus, 900 cycles is only one embodiment of the number of cycles that are counted which may be more or less in alternative embodiments. Once the cycles reach 900 or more, the LED indicator light 37 or alarm is activated at step 549 to indicate to a user or owner that additional soap will be needed. Also, part of the flow chart B is the battery sensor at step 550 that checks to see if the battery level is less than a predetermined voltage level, e.g., 4.85V. If it is, then the LED indicator light 37 or alarm is activated at step 551 to indicate that the battery is low so that the battery may be recharged or replaced. If the battery level is not less than a predetermined voltage level, the soap is dispensed at step 546 without the LED indicator light 37 or alarm being activated. Again, it is noted that the battery voltage level and number of cycles that trigger the LED indicator light 37 or alarm to activate may vary in alternative embodiments, yet fall within the scope of the subject matter of the claims below.

Recall that soap dispensing circuit 500 includes an example implementation for assembly control circuit 503.

FIGS. 33A–I constitutes exemplary schematic diagram 700 of soap dispenser circuit 500 of FIG. 31. As shown in FIG. 33A, the oscillator circuit 626 may include a standard LRC circuit and logic gate inventors to produce a system frequency (i.e., oscillation) signal as known in the art. This system frequency signal may be provided to the first frequency divider 627.

As depicted in FIGS. 33A–B, the first frequency divider 627 and the second frequency divider 628 may utilize the system frequency signal to produce outputs Q1–Q12, and Q13–Q24, respectively. The outputs Q1–Q12, and Q13–Q24 provide the required waveforms and timing signals for the TX and RX control circuit 610 (see FIG. 33C), the memory counter 620 (see FIG. 33F), the motor driver 614 (see FIG. 33G), the LED driver 629 (see FIG. 33H), and the tone driver 625 (see FIG. 33I). The first 527 and second 528 frequency dividers may be any standard logic counter or programmable logic array.

In FIG. 33C, an example implementation of TX and RX control circuit 610 may be shown. The TX and RX control circuit 610 utilizes standard logic gates IC3–IC7 and IC10 to provide a signal bias via a standard transistor 517 to the IR detector 502 when the appropriate logic may be present. The standard transistor 517 may be electrically connected to a voltage source 518 (e.g., 5V) and IR detector 502 as shown in FIG. 31. The standard transistor 517 acts like a switch. When the signal bias from the TX and RX control circuit may be present, the standard transistor may be gated or switched closed allowing the voltage source 518 to prompt the IR detector 502 to operate. It may be noted that the IR detector 502 may be electrically connected to a ground 519 to properly control the flow of charge to the IR detector 502.

The TX and RX control circuit 610 also utilizes standard logic gates IC3–IC8, IC11, and IC13 to produce a transmit signal based on waveform and timing outputs (i.e., Q2, Q4, Q6, and Q8) from the first frequency divider 627, FIG. 33A. In one implementation, the transmit signal may be a three pulse signal that prompts the IR emitter 501 to emit a corresponding pulsed IR signal for each cycle of the system frequency signal. In addition, the TX and RX control circuit 610 utilizes standard logic gates IC3–IC9, IC1–IC12, and IC14–IC21 to produce a clock signal that synchronizes the detection of a group of continuous pulses (e.g., three continuous pulses) by the receiver circuit 613 (see FIG. 33D).

In FIG. 33D, an example implementation of receiver circuit 613 may be shown. The receiver circuit 613 includes three D-type flip-flops 6131, 6132, and 6133 for latching three continuous pulses from the IR detector 502. Other two state logic devices such as SR flip-flops, JK flip-flops, or resettable bit memory device may be used in alternative embodiments to latch a detected pulse. When three continuous pulses (which may be more or less in other embodiments) are received by the receiver circuit 613, the receiver circuit 613 generates a pulse detected signal that may be provided to the motor driver 614 circuit. Three pulses allows the soap dispenser circuit 500 to distinguish between an actual user, and other elements accidentally passing in front of emitter 501. Upon receiving the pulse detected signal and the waveform and timing signal Q16, the motor driver 614 circuit generates a "dispense soap" signal (i.e., count signal in FIGS. 33E and 33F) that results in the motor 49 dispensing soap for a predetermined period.

The memory counter 620, FIG. 33F, also receives the dispense soap signal from the motor driver 614 circuit via an electrical connection through switch control circuit 621. The memory counter 520, which may be any standard logic counter or programmable logic array, increments an internal counter upon receiving the dispense soap signal from the motor driver 614 circuit. The memory counter 620, thus, keeps track of the number of cycles (i.e., times soap may be dispensed). Based on a number of cycles selection (e.g., 960 or 1200 cycles), the memory counter 620 sends an end signal to the LED driver 625, FIG. 33H, and the tone driver 625, FIG. 33I when the number of cycles selection may be reached to signal that the soap dispenser assembly must be refilled. Upon receiving the end signal, the LED driver 625 sets an indicator light embedded in electric eye sensor unit 36 and visible through lens 34 (FIG. 29). Also, upon receiving the end signal, the tone driver 625 activates an alarm via speaker 507. Note that the dispenser 10 will continue to operate after the indicator light or the alarm have been activated.

The switch control circuit 621 that controls three [?] switches, in this embodiment, including a test switch 521, a reset switch 522 and a counter switch 523. These switches are conventional switches that are opened and closed to provide discharge of electrical current to ground depending on which operation (e.g., testing, resetting or counting) may be needed. Using the switch control circuit 521, and in conjunction with the motor driver 514 and TX and RX control circuit 510, the memory counter 520 keeps track of the number of cycles (i.e. times soap may be dispensed) and sends a signal to the LED driver 525 and tone driver 525 when a certain number of cycles have occurred (e.g., 960 or 1200 cycles) so that an indicator light embedded in electric eye sensor unit 36 and visible through lens 34 (FIG. 29), or alarm (e.g., using speaker 507),may be activated to signal that the soap dispenser assembly must be refilled. Note that the dispenser 10 will continue to operate after the indicator light or alarm have been activated.

FIGS. 24, 25, 27 and 28 illustrate an embodiment of the reservoir module and pump assembly 16 described previously and adapted for use in automatic soap dispenser 10. The soap inlet tube 242, pump mechanism 65, actuator 174 and dispensing tube 68 all form a unitary assembly that may be discarded when the container 60 has been emptied of fluid soap. Therefore, a new pump mechanism 65 and tubes 68 and 242 may be furnished with each replacement module 16 installed in dispenser 10.

In the invention, to provide ease of installation of module 16, as will be explained, dispensing tube 68, actuator 174, pump mechanism 65 and intake tube 242 are all aligned on a common centerline, shown by the numeral 64 in FIGS. 2 and 24. Thus, when module 16 is rotated during installation and removal from motor housing and support assembly 14, all of the elements comprising reservoir module 16 rotate smoothly and substantially frictionless in their respective housings and passageways. This is of particular importance with regard to the integrity of elongated dispensing tube 68, which follows an actuator path in passageway 66 of spout 24 (FIG. 2). The rotation of reservoir module 16 during installation and removal causes bent tube 68 to rotate about its own axis, shown as 67 in FIG. 5. However, since the rotation takes place around tube 68's own axis, the entire tube rotates substantially freely without any significant compressive or tensile stress being applied to the dispensing tube 68.

Another factor resulting from the single centerline construction of reservoir module 16 is that actuator 174 may be used with a commonly available pump mechanism 65, without the need for any specially constructed or located pump assemblies. This obviously reduces the cost of reservoir module 16. Pump mechanism 65 is a self priming pump which delivers a predetermined dosage of fluid soap from tube end 70 of dispensing tube 68 (FIG. 3) upon each actuation of the motor 49 (FIG. 2). Note also that dispensing tube 68 moves reciprocally in spout passageway 66 with each operation of actuator 174, to provide advantages described below in conjunction with the operation of automatic soap dispenser. 10.

The installation of the fluid dispensing system 10 of the invention, as viewed in FIG. 2, is initiated by providing an appropriately sized aperture 22 in countertop 18 at a point adjacent the rim of a sink bowl (not shown) in the countertop 18. Support shaft 20, which is attached to spout and mounting shaft assembly 12 is inserted downward through aperture 32 until resilient pad 27 beneath base portion 25 of spout 24 abuts the upper surface 29 of countertop 18. Nut 38 and lock washer 40 are then installed over lower portion 94 of support shaft 20, with connecting wire 50 extending through the central opening of nut 38 and lock washer 40. Nut 38 and lock washer 40 tightly abut the underside 33 of countertop 18, with spout 24 being previously rotated such that the spout opening 31 is directed to the sink bowl.

Motor housing and support assembly 14 is then attached to support shaft 20 by placing interior portion 106 (FIGS. 2, 7) of assembly 14 over attachment shaft 100 such that splines 102 and grooves 104 mate along their respective lengths. Prior to this step, sidewall 118 of shank clip 42 is partially inserted into pump housing groove 148 on assembly 14, and is held in the position shown in FIG. 12A. When installing assembly 14, motor and actuator mechanism housing 46 may initially abut against the underside of the sink bowl, or interfere with undersink plumbing or other hardware, fixtures or wires. This problem, if it occurs, may be relieved by removing assembly 14 from attachment shaft 100, rotating assembly 14 whereby motor housing 46 does not interfere with any other elements, and re-insert interior portion 106 of assembly 14 over attachment shaft 100 until the splines 102 and grooves 104 mate again.

In the illustrated embodiment, assembly 14 may be rotated in increments of thirty degrees. When assembly 14 is in its appropriate position relative to support shaft 20, shank clip 42 is manually pushed inward such that sidewall 116 is fully inserted into shaft groove 108 on attachment shaft 100 as circular portion 126 (FIG. 11) engages the bottom 109 of shaft groove 108 and securely holds motor housing and support assembly 14 to support shaft 20. In case it becomes necessary to remove assembly 14 from support shaft 20, the process is reversed whereby shank clip 42 is laterally moved out of shaft groove 108 and pump housing groove 148, releasing assembly 14 from support shaft 20.

Figure 33:
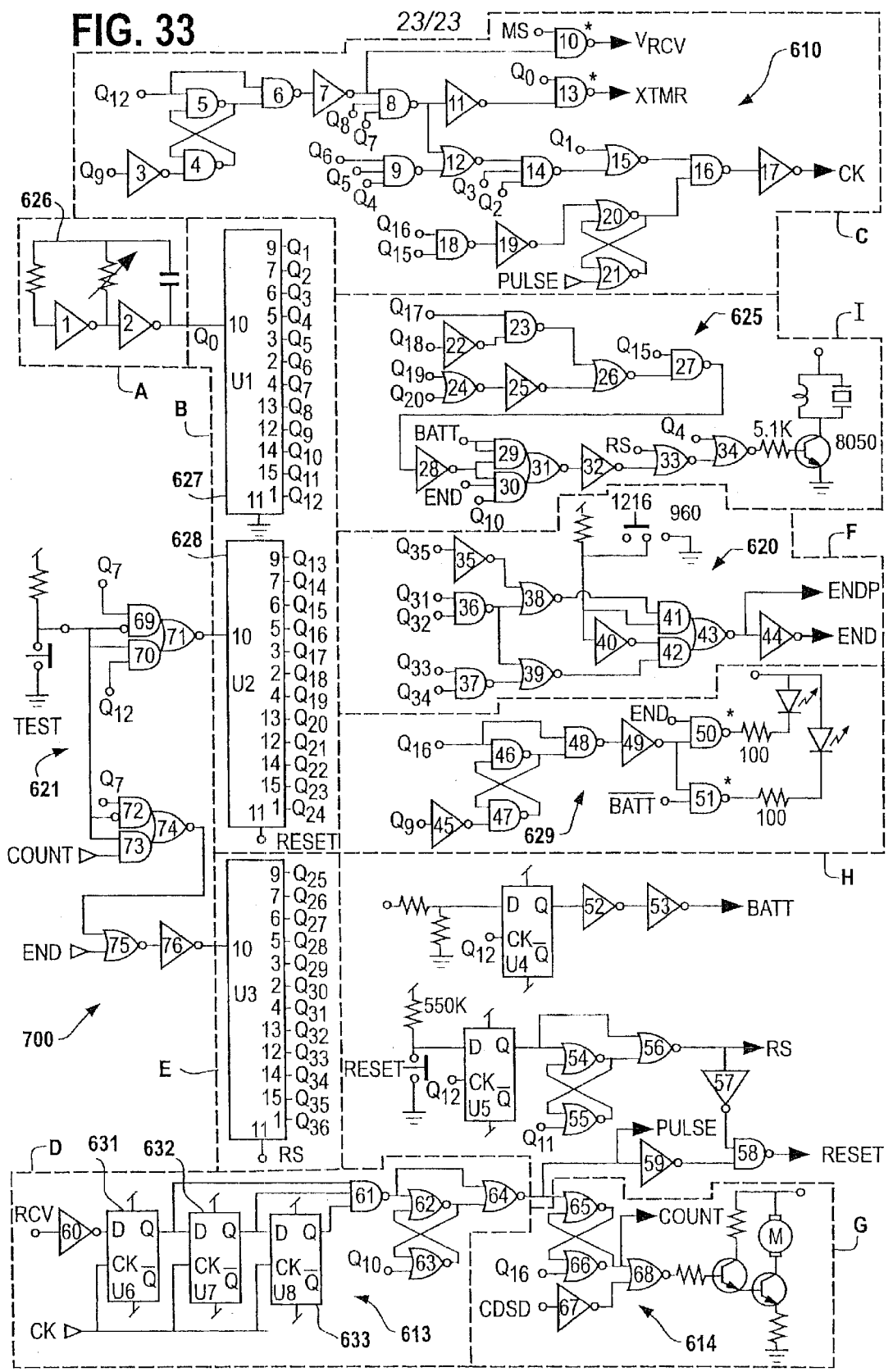
FIG. 33 is an exemplary schematic diagram of the soap dispenser circuit of FIG. 31.

After motor housing and support assembly 14 is properly attached to support shaft 20, as described above, wire 50 (FIG. 1) is attached to a socket (not shown) in motor housing 46 which connects wire 50 to motor 49 and the circuitry shown in FIGS. 31 and 33 for operation of electric eye sensor unit 36 and motor 49. Also, battery pack 52 (FIG. 2) including an appropriate number of electric batteries, is attached to a cabinet wall, facility wall, or other fixture element (not shown), and wire 54 is connected to wire 56 through releasable attachment element 58.

The installation of the fluid soap reservoir and pump assembly into fluid dispensing system 10 is initiated by aligning the tube end 70 of dispensing tube 68 with the centrally disposed aperture 296 (FIG. 14) formed where assembly 14 necks inward. The beveled sides 298 of aperture 296 assist in guiding dispensing tube 68 upward through aperture 296.

Container 60, with dispensing tube 68, actuator 174 and pump mechanism 65 attached, is moved upward, feeding dispensing tube 68 into passageway 66 of spout 24. Container 60 continues to be moved upward until top surface 180 (FIG. 14) of actuator 174 abuts limiting surface 182 of assembly 14, preventing further upward movement of container 60. At this juncture, dispensing tube 68 is fully inserted in passageway 66 of spout 24, and the tube end 70 of the dispensing tube extends out of the spout opening 31 (FIG. 2) a short distance, such that tube end 70 of dispensing tube 68 is not visible to a user in part due to indented portion 72 of curved dispensing portion 28 of spout 20 (FIG. 3).

As reservoir module and pump assembly 16 is moved upward, tabs 292 on neck 246 (FIG. 27) pass into opening 262 in mounting clip 48, with each tab 292 moving through spaces 288 formed between protuberances 286 until each tab 292 is adjacent groove 282 in mounting clip 48. As upward movement of container 60 is halted, container 60 is rotated in either direction, compelling tabs 292 to be positioned in groove 282 adjacent to protuberances 286. Stop member 285 abuts one of the tabs 292 of container 60 to control rotation motion of the container 60. Friction surfaces 290 on an upward side of some or all of protuberances 286 apply pressure to tabs 292 to hold container 60 and module 16 securely, but removably in proper contact with motor housing and support assembly 14. Here, bumps 295 (FIG. 27) may be disposed in indentations 291 (FIG. 21).

To remove an empty reservoir module 16 from assembly 14, the container 60 is rotated in an opposite direction from that described above until tabs 292 align with spaces 288 in mounting clip 48. The container 60 is then lowered, withdrawing dispensing tube 68 from passage 66 in spout 24, and withdrawing actuator 174 and pump assembly 65 from motor housing and support assembly 16. A full reservoir module is then installed, as set forth above. Several priming pump actuations may automatically occur (FIG. 32) to raise an initial quantity of soap from container 60 up into dispensing tube 68.

Once properly installed, operation of the fluid dispensing system 10 is initiated by a user inserting his or her hands under indented outlet 30 of spout 24. Electric eye sensor 36 detects the presence of the hands, and sends a signal, as previously described, to actuator motor 49. Gear reduction train 51 drives pump hammer 53 in a clockwise direction, as viewed in FIG. 2, whereby actuator arms 162, 164 initially move toward flange 176 of actuator 174 (FIG. 15A), and the upper portion 190 of the actuator 174 falls into open space 172 between actuator arms 164 and 166 of pump hammer 53. The actuator arms 164, 166 engage the upper surface of actuator flange 176 (FIG. 15B) and drive actuator 174 downward, as viewed in FIG. 15C. In the illustrated embodiment, and by way of example only, actuator 174 moves downward a distance of 0.280 inches. This downward movement of actuator 174 causes elongated dispensing tube 68 to withdraw the same distance into spout 24 and passageway 66. In the illustrated embodiment, the tube end 70 of dispensing tube 68 remains outside of the spout opening 31 in spout 24 in the withdrawn position.

As actuator 174 moves downward under the influence of pump hammer 53, a measured dosage of fluid soap is dispensed from tube end 70 of elongated dispensing tube 68, even as tube 68 is moving to its withdrawn position. Referring to FIG. 20, pump mechanism 65, in the illustrated embodiment, is a self-priming pump in which the pump mechanism and dispensing tube 242 are filled with fluid soap prior to actuation of the pump mechanism. As actuator 174 moves downward, pump mechanism 65 forces upward the fluid soap in the pump mechanism, and compresses spring 236. Ball cocks 206 and 232 move upward, causing additional fluid soap to be advanced through inlet tube 242, past ball cock 232, and into chamber 218. Ball cock 206 rises up, but its upward movement is limited when ball cock 206 abuts landing 204 of timing shaft 196.

As pump hammer 53 reaches its limit of clockwise rotation, the motor 49 stalls, and spring 236 (FIG. 20) forces pump mechanism 65, actuator 174 and dispensing tube 68 in an upward direction, causing fluid soap to fill the interior of pump mechanism 65 and dispensing tube 68. Ball cock 206 moves to its closed position over aperture 214. The time ball cock 206 takes to move from landing 204 to V-shaped trough 216 determines the amount of soap dispensed in a single actuation of pump mechanism 65.

Figure 18:
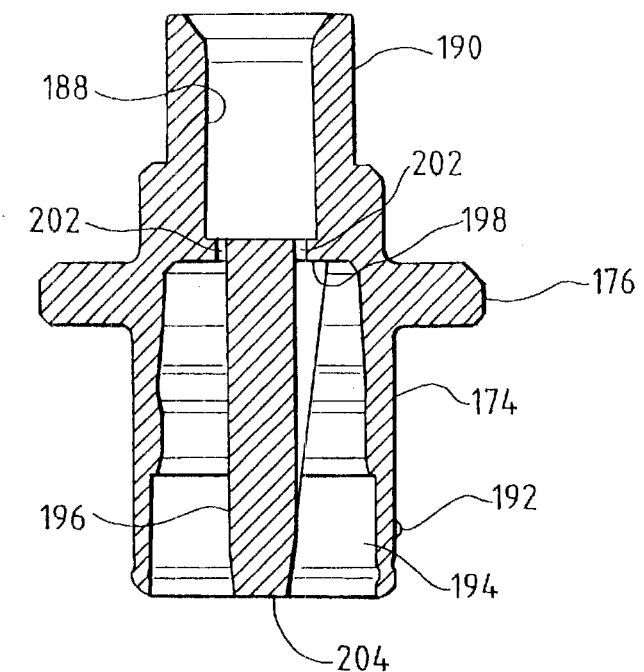
FIG. 18 is a cross-sectional elevation view of the actuator of the invention, taken along line 18—18 in FIG. 16.
Figure 19:
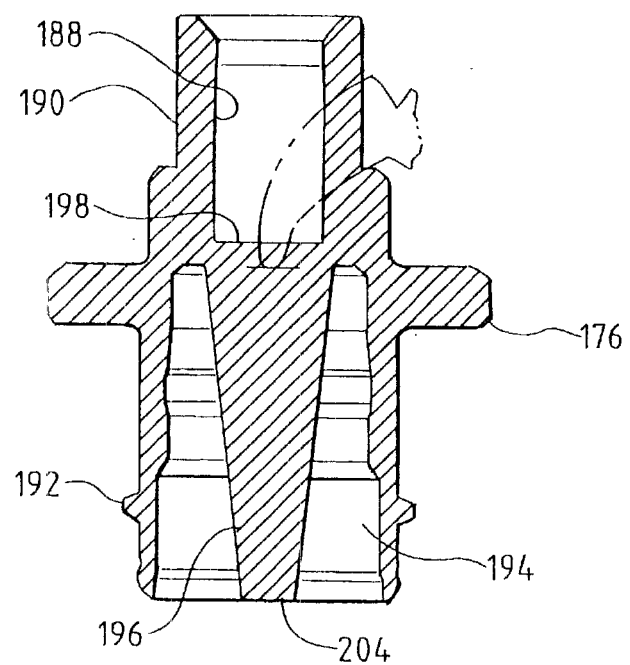
FIG. 19 is a cross-sectional elevation view of the actuator of the invention, taken along line 19—19 in FIG. 16.

Referring to FIG. 18, when soap is being dispensed by pump mechanism 65, fluid soap passes through openings 202 and around timing shaft 196 in actuator 174. Upon actuation of pump mechanism 65, fluid soap is dispensed from tube end 70 of tube 68 in a continuous stream as the tube 68 is retracted toward the spout 24. When the motor 49 stalls, as described above, spring 236 (FIG. 20), which was compressed during soap delivery, causes pump chamber 218 to expand as the dispensing tube 68 returns back out of the spout opening 31 in the spout 24. The combination of the expansion of pump chamber 218 and the forward motion of the dispensing tube causes the fluid soap exiting the tube end 70 to be sucked back in at the return of tube 68. This catches a string of soap in the tube 68 which would otherwise drip down after the main soap delivery function. This mode of operation also prevents dripping and residue buildup between uses and cleanings of the soap dispenser.

The foregoing description of illustrated embodiment of the invention has been presented for purposes of description, and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated. It is intended that the scope of the invention not be limited to specification, but be defined by the subject matter of the claims set forth below.

What is claimed is:

1. A reservoir module for insertion and removal as a unit from a fluid dispensing system, the reservoir module comprising:
   a container adapted to hold fluid material to be dispensed by the dispensing system, the container defining a central axis and having a top portion;
   an aperture in the top portion of the container, the aperture located on the central axis of the container;
   a fluid pump mechanism mounted on the top portion of the container and disposed in alignment with the aperture; and
   a delivery tube attached to an upper portion of the fluid pump mechanism, the delivery tube disposed in alignment with the central axis of the container.

2. The reservoir module of claim 1 wherein the delivery tube is elongated.

3. The reservoir of claim 1 wherein the fluid pump mechanism includes an actuator having a flange, the flange disposed off center relative to the central axis of the container.

4. The reservoir module of claim 1 wherein the fluid pump mechanism includes an actuator which dispenses the fluid material from the container through the pump mechanism to the delivery tube upon actuation of the actuator by the pump mechanism.

5. A reservoir module for a dispensing system, the reservoir module comprising:
   a container adapted to hold fluid material to be dispensed by the dispensing system, the container defining a central axis and having a top portion;
   an aperture in the top portion of the container, the aperture located with respect to the central axis of the container;
   a fluid pump mechanism mounted on the top portion of the container and disposed in alignment with the aperture;
   an elongated delivery tube attached to an upper portion of the fluid pump mechanism, the delivery tube disposed in alignment with the central axis of the container; and
   a timing shaft that is adapted to permit fluid material to be advanced from the pump mechanism through a central portion of a pump actuator and to the centrally disposed delivery tube upon actuation of the actuator.

6. A dispensing system for fluid material, the dispensing system comprising:
   a dispensing spout;
   a housing operatively connected to the dispensing spout;
   a reservoir module having a central axis, the housing adapted to removably receive and hold the reservoir module in communication with the dispensing spout; and
   a delivery tube mounted on the reservoir module and disposed in alignment with the central axis.

7. The dispensing system of claim 6 wherein the delivery tube is disposed in the dispensing spout when the reservoir module is held by the housing.

8. The dispensing system of claim 7 further comprising:
   a pump mechanism, wherein the pump mechanism includes a means for selectively activating the pump mechanism, wherein the delivery tube is adapted to move an incremental amount from a first position to a second position in the dispensing spout when the pump mechanism is actuated.

9. The dispensing system of claim 8 wherein the means for selectively actuating is an actuator and wherein the pump mechanism includes a biasing element, wherein the biasing element is adapted to return the delivery tube to the first position in the dispensing spout upon a completion of the actuation of the pump mechanism.

10. A dispensing system for fluid material, the dispensing system comprising:
    a dispensing spout;
    a housing that includes at least one internal groove, wherein the internal groove is horizontally and circumferentially disposed at a lower end of the housing, wherein the housing further includes a first opening that is disposed adjacent the internal groove, and where the housing is operatively connected to the dispensing spout;
    a reservoir module having a central axis, wherein the reservoir module includes a centrally disposed second opening in a top portion of the reservoir module such that the second opening is disposed in the first opening when the reservoir module is held by the housing, the housing adapted to removably receive and hold the reservoir module in communication with the dispensing spout; and
    a delivery tube mounted on the reservoir module and disposed in alignment with the central axis.

11. The dispensing system of claim 10 wherein the reservoir module includes a neck portion adjacent to the second opening, at least one flange element extending outwardly from the neck portion, wherein the at least one flange extends into the at least one groove of the housing to releasably hold the reservoir module to the housing when the reservoir module is held by the housing.

12. The dispensing system of claim 11 wherein the internal groove in the housing includes at least one downwardly extending slot through which the at least one flange moves when the reservoir module is one of installed and removed relative to the housing.

13. The dispensing system of claim 6 wherein the delivery tube is extended into the dispensing spout when the reservoir module is installed in the housing, and the delivery tube is withdrawn from the dispensing spout when the reservoir module is removed from the housing.

14. The dispensing system of claim 6 wherein the reservoir module includes a pump mechanism actuator operatively connected to the pump mechanism to selectively actuate the pump mechanism and wherein the housing includes a drive mechanism operatively connected to the pump mechanism actuator, the drive mechanism moving the pump mechanism actuator upon the detection of the presence of a user of the dispensing system.

15. A method to dispense fluid soap from a dispensing system, wherein the dispensing system includes a spout, a dispensing tube movably disposed in the spout, and a fluid soap container having a pump mechanism attached to the dispensing tube, the method comprising:

a) sensing a hand of a user;

b) activating the pump mechanism upon sensing the hand;

c) in response to activating the pump mechanism, moving the dispensing tube in a first direction relative to the spout to expel fluid soap from the dispensing tube; and d) moving the dispensing tube in a second direction relative to the spout upon completion of activating the pump mechanism.

16. The method of claim 15, wherein sensing a hand of a user includes detecting an infrared signal that is reflected off the hand of the user.

17. A method to dispense fluid soap from a dispensing system, wherein the dispensing system includes a spout, a dispensing tube movably disposed in the spout, and a fluid soap container having a pump mechanism attached to the dispensing tube, the method comprising:

a) sensing a hand of a user;

b) activating the pump mechanism upon sensing the hand;

c) in response to activating the pump mechanism, moving the dispensing tube in a first direction relative to the spout to expel fluid soap from the dispensing tube, wherein moving the dispensing tube in a first direction relative to the spout includes activating a torque of a motor to rotate an actuator arm of a pump hammer so that the actuator arm contacts a flange on a pump actuator and urges the pump actuator downward to overcome a spring bias; and d) moving the dispensing tube in a second direction relative to the spout upon completion of activating the pump mechanism.

18. The method of claim 17 wherein moving the dispensing tube in a second direction relative to the spout includes stalling the motor so that the spring bias overcomes the torque of the motor to urge the pump actuator upwards.

19. A reservoir module for use with a fluid dispensing system, the reservoir module comprising:

a container defining a longitudinal axis;

a pump mechanism defining a center and attached to the container;

a pump actuator defining a center and coupled to the pump mechanism; and a delivery tube having a lower end and defining a center and an axis that follows the center of the delivery tube, wherein the delivery tube extends at the lower end from the pump actuator and wherein the longitudinal axis of the container is aligned through the center of the pump mechanism, the center of the pump actuator, and the axis of the delivery tube at least at the lower end of the delivery tube.

20. The reservoir module of claim 19, wherein the pump actuator includes a flange that extends radially outward from the pump actuator.

21. A reservoir module for use with a fluid dispensing system, the reservoir module comprising:

a container defining a longitudinal axis, wherein the container includes a top closure and a neck disposed above the top closure, the neck having at least two tabs that extend radially from the neck;

a pump mechanism defining a center and coupled to the container;

a pump actuator defining a center and coupled to the pump mechanism; and a delivery tube having a lower end and defining a center and an axis that follows the center of the delivery tube, wherein-the delivery tube extends at the lower end from the pump actuator and wherein the longitudinal axis of the container is aligned through the center of the pump mechanism, the center of the pump actuator, and the axis of the delivery tube at least at the lower end of the delivery tube.

22. The reservoir module of claim 21, wherein the at least two tabs are four tabs symmetrically disposed about the center longitudinal axis.

23. The reservoir module of claim 22 wherein the container includes at least one bump disposed below a tab.

24. A reservoir module for use with a fluid dispensing system, the reservoir module comprising:

a container defining a longitudinal axis;

a pump mechanism defining a center and coupled to the container and wherein the pump mechanism includes a stationary housing coupled to the container by a ferrule so as to extend into the container, the stationary housing having a first aperture over which a first ball cock resides, and wherein the pump mechanism further includes an intake tube having a second aperture over which a second ball cock resides and having a circular wall disposed within an interior of the stationary housing, wherein the circular wall is resilient, extends outwardly form the center of the pump mechanism, and wherein the pump mechanism includes a pump sealing member coupled to the interior of the stationary housing so as to retain the circular wall within the interior of the stationary housing, and wherein the pump mechanism includes a spring disposed within the interior of the stationary housing so as to bias the circular wall against the pump sealing member;

a pump actuator defining a center and coupled to the pump mechanism; and a delivery tube having a lower end and defining a center and an axis that follows the center of the delivery tube, wherein the delivery tube extends at the lower end from the pump actuator and wherein the longitudinal axis of the container is aligned through the center of the pump mechanism, the center of the pump actuator, and the axis of the delivery tube at least at the lower end of the delivery tube.

25. The reservoir module of claim 24, further comprising:

an inlet tube disposed within the container and coupled to the stationary housing.

26. A reservoir module for use with a fluid dispensing system, the reservoir module comprising:

a container defining a longitudinal axis;

a pump mechanism defining a center and coupled to the container;

a pump actuator defining a center and coupled to the pump mechanism wherein the pump actuator defines an opening and includes a timing shaft disposed in the opening; and a delivery tube having a lower end and defining a center and an axis that follows the center of the delivery tube, wherein the delivery tube extends at the lower end from the pump actuator and wherein the longitudinal axis of the container is aligned through the center of the pump mechanism, the center of the pump actuator, and the axis of the delivery tube at least at the lower end of the delivery tube.

27. The reservoir module of claim 26, wherein the timing shaft includes a plurality of blades that extend radially outward from the center of the pump actuator.

28. A fluid dispensing system, comprising:

a reservoir module having a container, the container defining a longitudinal axis, the reservoir module further having a pump mechanism defining a center and attached to the container, a pump actuator defining a center and coupled to the pump mechanism, and a delivery tube having a lower end and defining a center and an axis that follows the center of the delivery tube, wherein the delivery tube extends at the lower end from the pump actuator and wherein the longitudinal axis of the container is aligned through the center of the pump mechanism, the center of the pump actuator, and the axis of the delivery tube at least at the lower end of the delivery tube; and a spout and mounting shaft assembly, wherein the delivery tube is disposed within the spout and mounting shaft assembly.

29. A fluid dispensing system, comprising:

a reservoir module having a container, the container defining a longitudinal axis, the reservoir module further having a pump mechanism defining a center and coupled to the container, a pump actuator defining a center and coupled to the pump mechanism, and a delivery tube having a lower end and defining a center and an axis that follows the center of the delivery tube, wherein the delivery tube extends at the lower end from the pump actuator and wherein the longitudinal axis of the container is aligned through the center of the pump mechanism, the center of the pump actuator, and the axis of the delivery tube at least at the lower end of the delivery tube;

a spout and mounting shaft assembly, wherein the delivery tube is disposed within the spout and mounting shaft assembly; and a motor housing and support assembly coupled between the reservoir module and the spout and mounting shaft assembly.

30. The fluid dispensing system of claim 29, wherein the reservoir module includes a pump actuator having a flange and wherein the motor housing and support assembly includes a pump hammer that is disposed to interact with the flange of the pump actuator.

31. The fluid dispensing system of claim 29, wherein the pump actuator defines an opening and includes a timing shaft disposed in the opening, wherein the timing shaft includes a plurality of blades that extend radially outward from the center of the pump actuator.

32. The fluid dispensing system of claim 29, wherein the spout and mounting shaft assembly includes a spout defining a spout tip, the spout having an indented outlet that extends within the spout from the spout tip to define a spout opening, wherein the delivery tube defines a tube end, the tube end having a first position and a second position, wherein the tube end resides within the indented outlet in the first position and the second position.

33. The fluid dispensing system of claim 32, wherein the spout and mounting shaft assembly further includes an electric eye sensor residing in an opening in the spout.

34. The fluid dispensing system of claim 33, wherein the electric eye sensor includes a signal emitter, a signal receiver communicatively coupled to a motor disposed in the motor housing and support assembly, a speaker, and an indicator light.

35. The fluid dispensing system of claim 33, wherein at least one of the speaker and the indicator light are adapted to emit at least one of a low fluid signal and a low power signal.

36. The fluid dispensing system of claim 29, wherein the spout and mounting shaft assembly includes a spout and a support shaft coupled to the spout, wherein the motor housing and support assembly includes a pump housing, wherein the support shaft and the pump housing are coupled to one another by a plurality of splines and grooves.

37. The fluid dispensing system of claim 36, wherein the plurality of splines are disposed on an end of the support shaft.

38. The fluid dispensing system of claim 37, wherein each of the plurality of splines are disposed at an angle of thirty degrees from an adjacent spline.

39. The fluid dispensing system of claim 29, wherein the spout and mounting shaft assembly includes an internal passageway disposed within the spout between the spout opening and the support shaft.

* * * * *